United States Patent
Egan et al.

(10) Patent No.: US 9,988,676 B2
(45) Date of Patent: Jun. 5, 2018

(54) MICROFLUIDIC CARTRIDGE

(71) Applicants: LOCKHEED MARTIN CORPORATION, Bethesda, MD (US); MICROLAB DIAGNOSTICS, INC., Charlottesville, VA (US)

(72) Inventors: Michael E. Egan, Charlottesville, VA (US); Brian Root, Charlottesville, VA (US); Orion N. Scott, Charlottesville, VA (US); Douglas J. South, Rockville, MD (US); Joan M. Bienvenue, Fredericksburg, VA (US); Paul Kinnon, Solana Beach, CA (US); James Landers, Charlottesville, VA (US); David Saul, Auckland (NZ); An-Chi Tsuei, Charlottesville, VA (US); Jason Hayes, Heathmont (AU); Matthew Springer, West Melbourne (AU); Matthew Solomon, Hughesdale (AU); Peter Van Ruijven, Glen Waverley (AU)

(73) Assignee: LEIDOS INNOVATIONS TECHNOLOGY, INC., Gaithersburg, MD (US)

( * ) Notice: Subject to any disclaimer, the term of this patent is extended or adjusted under 35 U.S.C. 154(b) by 121 days.

(21) Appl. No.: 14/744,889

(22) Filed: Jun. 19, 2015

(65) Prior Publication Data

US 2015/0284775 A1    Oct. 8, 2015

Related U.S. Application Data

(62) Division of application No. 13/773,350, filed on Feb. 21, 2013, now Pat. No. 9,322,054.
(Continued)

(51) Int. Cl.
*C12M 1/00* (2006.01)
*C12Q 1/68* (2018.01)
(Continued)

(52) U.S. Cl.
CPC .......... *C12Q 1/686* (2013.01); *B01L 3/50273* (2013.01); *B01L 3/502715* (2013.01); *B01L 3/502723* (2013.01); *B01L 3/502753* (2013.01); *B01L 7/52* (2013.01); *C12P 19/34* (2013.01); *C12Q 1/6844* (2013.01); *C12Q 1/6853* (2013.01); *G01N 21/75* (2013.01); *B01L 3/5029* (2013.01); *B01L 3/502738* (2013.01); *B01L 3/502784* (2013.01); *B01L 2200/027* (2013.01); *B01L 2200/04* (2013.01); *B01L 2200/0684* (2013.01); *B01L 2200/0689* (2013.01); *B01L 2200/10* (2013.01); *B01L 2200/148* (2013.01); *B01L 2200/16* (2013.01); *B01L 2300/044* (2013.01); *B01L 2300/0654* (2013.01); *B01L 2300/0663* (2013.01); *B01L 2300/0672* (2013.01); *B01L 2300/0816* (2013.01); *B01L 2300/0832* (2013.01); *B01L 2300/0864* (2013.01); *B01L 2300/0867* (2013.01); *B01L 2300/0877* (2013.01); *B01L 2300/14* (2013.01); *B01L 2300/161* (2013.01); *B01L 2300/18* (2013.01); *B01L 2300/1872* (2013.01); *B01L 2400/049* (2013.01); *B01L 2400/0487* (2013.01); *B01L 2400/0683* (2013.01); *B01L 2400/088* (2013.01)

(58) Field of Classification Search
CPC .......... B01L 2200/027; B01L 2200/04; B01L 2200/0684; B01L 2200/0689; B01L 2200/10; B01L 2200/148; B01L 2200/16; B01L 2300/044; B01L 2300/0654; B01L 2300/0663; B01L 2300/0672; B01L 2300/0816; B01L 2300/0832
USPC ...................................... 435/283.1
See application file for complete search history.

(56) References Cited

U.S. PATENT DOCUMENTS 2,654,387 A    10/1953 Innes
3,357,233 A    12/1967 Roof
(Continued)

FOREIGN PATENT DOCUMENTS

DE    195 49 052 A1    7/1996
EP    0 356 160 A2    2/1990
(Continued)

OTHER PUBLICATIONS

Jun. 30, 2010 International Search Report issued in International Application No. PCT/US2010/026791.
(Continued)

*Primary Examiner* — Cynthia B Wilder
(74) *Attorney, Agent, or Firm* — Oblon, McClelland, Maier & Neustadt, L.L.P.

(57) ABSTRACT

A microfluidic cartridge can include at least one nucleic acid analysis portion. Each nucleic acid analysis portion can include a fluidic network being configured for micro-liter volumes or less, a sample input at the beginning of the fluidic network, a plurality of vent ports and fluidic channels in the fluidic network configured to effectuate hydrodynamic movement within the fluidic network, an extraction mixture reservoir in the fluidic network, a mixing chamber in the fluidic network, an amplification chamber in the fluidic network, and a separation channel in the fluidic network. A nucleic acid analyzer can be capable of performing nucleic acid analysis using the microfluidic cartridge. A nucleic acid analysis method can be performed using the microfluidic cartridge.

12 Claims, 14 Drawing Sheets

Related U.S. Application Data

(60) Provisional application No. 61/601,937, filed on Feb. 22, 2012.

(51) Int. Cl.
   *G01N 21/75* (2006.01)
   *C12P 19/34* (2006.01)
   *B01L 3/00* (2006.01)
   *B01L 7/00* (2006.01)

(56) References Cited

U.S. PATENT DOCUMENTS

| | | |
|---|---|---|
| 3,404,869 A | 10/1968 | Harder |
| 3,459,407 A | 8/1969 | Halzehurst et al. |
| 3,799,742 A | 3/1974 | Coleman |
| 3,857,551 A | 12/1974 | Troy |
| 3,918,908 A | 11/1975 | Moyer et al. |
| 3,924,989 A | 12/1975 | Althausen et al. |
| 3,927,868 A | 12/1975 | Moore |
| 4,088,448 A | 5/1978 | Lilja et al. |
| 4,390,403 A | 6/1983 | Batchelder |
| 4,443,408 A | 4/1984 | Mintz |
| 4,534,659 A | 8/1985 | Dourdeville et al. |
| 4,554,839 A | 11/1985 | Hwewtt et al. |
| 4,675,300 A | 6/1987 | Zare et al. |
| 4,680,201 A | 7/1987 | Hjerten |
| 4,737,464 A | 4/1988 | McConnell et al. |
| 4,740,708 A | 4/1988 | Batchelder |
| 4,756,884 A | 7/1988 | Hillman |
| 4,790,640 A | 12/1988 | Nason |
| 4,849,340 A | 7/1989 | Oberhardt |
| 4,908,112 A | 3/1990 | Pace |
| 4,909,919 A | 3/1990 | Morris et al. |
| 4,952,518 A | 8/1990 | Johnson et al. |
| 4,963,498 A | 10/1990 | Hillman |
| 4,978,503 A | 12/1990 | Shanks et al. |
| 5,039,617 A | 8/1991 | McDonald et al. |
| 5,073,239 A | 12/1991 | Hjerten |
| 5,077,017 A | 12/1991 | Gorin et al. |
| 5,089,111 A | 2/1992 | Zhu et al. |
| 5,092,973 A | 3/1992 | Zare et al. |
| 5,094,793 A | 3/1992 | Schrenk et al. |
| 5,096,554 A | 3/1992 | Chin |
| 5,096,807 A | 3/1992 | Leaback |
| 5,100,627 A | 3/1992 | Buican et al. |
| 5,108,703 A | 4/1992 | Pfost et al. |
| 5,110,431 A | 5/1992 | Moring |
| 5,112,460 A | 5/1992 | Karger et al. |
| 5,122,248 A | 6/1992 | Karger et al. |
| 5,126,022 A | 6/1992 | Soane et al. |
| 5,132,012 A | 7/1992 | Miura et al. |
| 5,140,161 A | 8/1992 | Hillman et al. |
| 5,141,621 A | 8/1992 | Zare et al. |
| 5,144,139 A | 9/1992 | Hillman et al. |
| 5,147,606 A | 9/1992 | Charlton et al. |
| 5,154,888 A | 10/1992 | Zander et al. |
| 5,164,598 A | 11/1992 | Hillman et al. |
| 5,165,292 A | 11/1992 | Prohaska |
| 5,171,132 A | 12/1992 | Miyazaki et al. |
| 5,171,534 A | 12/1992 | Smith et al. |
| 5,180,480 A | 1/1993 | Manz |
| 5,188,963 A | 2/1993 | Stapleton |
| 5,192,405 A | 3/1993 | Petersen et al. |
| 5,223,219 A | 6/1993 | Subramanian et al. |
| 5,225,163 A | 7/1993 | Andrews |
| 5,229,297 A | 7/1993 | Schnipelsky et al. |
| 5,242,606 A | 9/1993 | Braynin et al. |
| 5,250,263 A | 10/1993 | Manz |
| 5,253,981 A | 10/1993 | Yang et al. |
| 5,271,724 A | 12/1993 | Van Lintel |
| 5,274,240 A | 12/1993 | Mathies et al. |
| 5,277,556 A | 1/1994 | Van Lintel |
| 5,278,048 A | 1/1994 | Parce et al. |
| 5,288,463 A | 2/1994 | Chemelli |
| 5,290,520 A | 3/1994 | Maystre et al. |
| 5,296,114 A | 3/1994 | Manz |
| 5,296,375 A | 3/1994 | Kricka et al. |
| 5,298,134 A | 3/1994 | Zare et al. |
| 5,304,487 A | 4/1994 | Wilding et al. |
| 5,314,593 A | 5/1994 | Swedberg |
| 5,318,680 A | 6/1994 | Fishman et al. |
| 5,320,139 A | 6/1994 | Paul et al. |
| 5,320,730 A | 6/1994 | Ewing et al. |
| 5,322,258 A | 6/1994 | Bosch et al. |
| 5,325,170 A | 6/1994 | Bornhop |
| 5,328,578 A | 7/1994 | Gordon |
| 5,338,427 A | 8/1994 | Shartle et al. |
| 5,346,999 A | 9/1994 | Cathcart et al. |
| 5,375,979 A | 12/1994 | Trah |
| 5,376,252 A | 12/1994 | Ekstrom et al. |
| 5,384,261 A | 1/1995 | Winkler et al. |
| 5,395,503 A | 3/1995 | Parce et al. |
| 5,410,030 A | 4/1995 | Yue et al. |
| 5,427,946 A | 6/1995 | Kricka et al. |
| 5,429,734 A | 7/1995 | Gajar et al. |
| 5,441,894 A | 8/1995 | Coleman et al. |
| 5,445,939 A | 8/1995 | Anderson |
| 5,460,709 A | 10/1995 | Sarrine et al. |
| 5,478,751 A | 12/1995 | Oosta et al. |
| 5,482,608 A | 1/1996 | Keely et al. |
| 5,486,335 A | 1/1996 | Wilding et al. |
| 5,496,697 A | 3/1996 | Parce et al. |
| 5,498,392 A | 3/1996 | Wilding et al. |
| 5,500,187 A | 3/1996 | Deoms et al. |
| 5,540,889 A | 7/1996 | Gordon et al. |
| 5,556,790 A | 9/1996 | Pettit |
| 5,560,811 A | 10/1996 | Brigges et al. |
| 5,571,410 A | 11/1996 | Swedberg et al. |
| 5,571,680 A | 11/1996 | Chen |
| 5,573,651 A | 11/1996 | Dasgupta et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,595,712 A | 1/1997 | Harbster et al. |
| 5,603,351 A | 2/1997 | Cherukuri et al. |
| 5,605,262 A | 2/1997 | Bond |
| 5,605,662 A | 2/1997 | Heller et al. |
| 5,627,643 A | 5/1997 | Birnbaum et al. |
| 5,632,876 A | 5/1997 | Zanzucchi et al. |
| 5,635,358 A | 6/1997 | Wilding et al. |
| 5,637,458 A | 6/1997 | Frankel et al. |
| 5,637,469 A | 6/1997 | Wilding et al. |
| 5,645,702 A | 7/1997 | Witt et al. |
| 5,650,075 A | 7/1997 | Haas et al. |
| 5,652,149 A | 7/1997 | Mileaf et al. |
| 5,658,723 A | 8/1997 | Oberhardt |
| 5,699,157 A | 12/1997 | Parce |
| 5,716,825 A | 2/1998 | Hancock et al. |
| 5,716,852 A | 2/1998 | Yager et al. |
| 5,726,026 A | 3/1998 | Wilding et al. |
| 5,726,404 A | 3/1998 | Brody |
| 5,731,212 A | 3/1998 | Gavin et al. |
| 5,750,015 A | 5/1998 | Soane et al. |
| 5,755,942 A | 5/1998 | Zanzucchi et al. |
| 5,770,029 A | 6/1998 | Nelson et al. |
| 5,773,298 A | 6/1998 | Lynggaard et al. |
| 5,779,868 A | 7/1998 | Parce et al. |
| 5,780,754 A | 7/1998 | Karlberg et al. |
| 5,783,397 A | 7/1998 | Hughes et al. |
| 5,788,927 A | 8/1998 | Farrell et al. |
| 5,800,690 A | 9/1998 | Chow et al. |
| 5,824,204 A | 10/1998 | Jerman |
| 5,830,681 A | 11/1998 | Hursting et al. |
| 5,833,926 A | 11/1998 | Wurzel et al. |
| 5,834,314 A | 11/1998 | Gates et al. |
| 5,842,787 A | 12/1998 | Kopf-Sill et al. |
| 5,846,396 A | 12/1998 | Zanzucchi et al. |
| 5,849,598 A | 12/1998 | Wilson et al. |
| 5,852,495 A | 12/1998 | Parce |
| 5,858,187 A | 1/1999 | Ramsey et al. |
| 5,858,188 A | 1/1999 | Soane et al. |
| 5,858,195 A | 1/1999 | Ramsey |
| 5,858,804 A | 1/1999 | Zanzucchi et al. |

(56) References Cited

U.S. PATENT DOCUMENTS

| | | | |
|---|---|---|---|
| 5,863,708 A | 1/1999 | Zanzucchi et al. |
| 5,863,801 A | 1/1999 | Southgate et al. |
| 5,869,004 A | 2/1999 | Parce et al. |
| 5,872,010 A | 2/1999 | Karger et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,900,130 A | 5/1999 | Benvegnu et al. |
| 5,919,070 A | 7/1999 | Khan et al. |
| 5,922,591 A * | 7/1999 | Anderson ........... B01F 11/0071 422/504 |
| 5,942,443 A | 8/1999 | Parce et al. |
| 5,945,334 A | 8/1999 | Basemer et al. |
| 5,948,227 A | 9/1999 | Dubrow |
| 5,948,684 A | 9/1999 | Weigl et al. |
| 5,955,028 A | 9/1999 | Chow |
| 5,955,030 A | 9/1999 | Pettit |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,965,001 A | 10/1999 | Chow et al. |
| 5,969,736 A | 10/1999 | Field et al. |
| 5,972,710 A | 10/1999 | Weigl et al. |
| 5,979,868 A | 11/1999 | Wu et al. |
| 5,980,704 A | 11/1999 | Crerukuri et al. |
| 5,985,119 A | 11/1999 | Zanzucchi et al. |
| 5,998,217 A | 12/1999 | Rao et al. |
| 6,001,299 A | 12/1999 | Ramsey |
| 6,010,607 A | 1/2000 | Ramsey |
| 6,010,608 A | 1/2000 | Ramsey |
| 6,012,902 A | 1/2000 | Parce |
| 6,033,546 A | 3/2000 | Ramsey |
| 6,054,277 A | 4/2000 | Furcht et al. |
| 6,062,261 A | 5/2000 | Jacobson et al. |
| 6,082,891 A | 7/2000 | Schubert et al. |
| 6,086,740 A | 7/2000 | Kennedy |
| 6,107,044 A | 8/2000 | Nikiforov |
| 6,110,343 A | 8/2000 | Ramsey et al. |
| 6,117,634 A | 9/2000 | Langmore et al. |
| 6,126,804 A | 10/2000 | Andresen |
| 6,132,580 A | 10/2000 | Mathies et al. |
| 6,132,685 A | 10/2000 | Kercso et al. |
| 6,134,950 A | 10/2000 | Forster et al. |
| 6,143,152 A | 11/2000 | Simpson et al. |
| 6,149,787 A | 11/2000 | Chow et al. |
| 6,149,815 A | 11/2000 | Sauter |
| 6,153,073 A | 11/2000 | Dubrow et al. |
| 6,156,181 A | 12/2000 | Parce et al. |
| 6,168,948 B1 | 1/2001 | Anderson et al. |
| 6,174,675 B1 | 1/2001 | Chow et al. |
| 6,176,991 B1 | 1/2001 | Nordman |
| 6,186,660 B1 | 2/2001 | Kopf-Sill et al. |
| 6,190,034 B1 | 2/2001 | Nielsen et al. |
| 6,197,595 B1 | 3/2001 | Anderson et al. |
| 6,210,882 B1 | 4/2001 | Landers et al. |
| 6,210,973 B1 | 4/2001 | Pettit |
| 6,213,151 B1 | 4/2001 | Jacobson et al. |
| 6,231,737 B1 | 5/2001 | Ramsey et al. |
| 6,235,175 B1 | 5/2001 | Dubrow et al. |
| 6,235,471 B1 | 5/2001 | Knapp et al. |
| 6,238,538 B1 | 5/2001 | Parce et al. |
| 6,261,431 B1 | 7/2001 | Mathies et al. |
| 6,267,858 B1 | 7/2001 | Parce et al. |
| 6,284,525 B1 | 9/2001 | Mate-Iies et al. |
| 6,287,850 B1 | 9/2001 | Besemer et al. |
| 6,303,343 B1 | 10/2001 | Kopf-Sill |
| 6,306,590 B1 | 10/2001 | Mehta et al. |
| 6,306,659 B1 | 10/2001 | Parce et al. |
| 6,316,201 B1 | 11/2001 | Nikiforov |
| 6,322,683 B1 | 11/2001 | Wolk et al. |
| 6,326,211 B1 | 12/2001 | Anderson et al. |
| 6,342,142 B1 | 1/2002 | Ramsey |
| 6,352,838 B1 | 3/2002 | Krulevitch et al. |
| 6,358,387 B1 | 3/2002 | Kopf-Sill et al. |
| 6,366,924 B1 | 4/2002 | Parce |
| 6,368,871 B1 | 4/2002 | Christel et al. |
| 6,372,484 B1 | 4/2002 | Ronchi et al. |
| 6,379,929 B1 | 4/2002 | Burns et al. |
| 6,395,232 B1 | 5/2002 | McBride |
| 6,399,025 B1 | 6/2002 | Chow |
| 6,399,365 B2 | 6/2002 | Besemer et al. |
| 6,403,338 B1 | 6/2002 | Knapp et al. |
| 6,408,878 B2 | 6/2002 | Unger et al. |
| 6,409,900 B1 | 6/2002 | Parce et al. |
| 6,413,401 B1 | 7/2002 | Chow et al. |
| 6,413,766 B2 | 7/2002 | Landers et al. |
| 6,420,143 B1 | 7/2002 | Kopf-Sill |
| 6,455,682 B1 | 9/2002 | Barron |
| 6,458,259 B1 | 10/2002 | Parce et al. |
| 6,475,363 B1 | 11/2002 | Ramsey |
| 6,479,299 B1 | 11/2002 | Parce et al. |
| 6,488,895 B1 | 12/2002 | Kennedy |
| 6,495,028 B1 | 12/2002 | Xu et al. |
| 6,506,609 B1 | 1/2003 | Wada et al. |
| 6,517,234 B1 | 2/2003 | Kopf-Sill et al. |
| 6,524,830 B2 | 2/2003 | Kopf-Sill |
| 6,534,009 B1 | 3/2003 | Yao |
| 6,534,013 B1 | 3/2003 | Kennedy |
| 6,544,734 B1 | 4/2003 | Briscoe et al. |
| 6,569,382 B1 | 5/2003 | Edman et al. |
| 6,576,459 B2 | 6/2003 | Miles et al. |
| 6,592,821 B1 | 7/2003 | Wada et al. |
| 6,602,472 B1 | 8/2003 | Zimmermann et al. |
| 6,632,619 B1 | 10/2003 | Harrison et al. |
| 6,642,000 B1 | 11/2003 | Strizhkov et al. |
| 6,649,358 B1 | 11/2003 | Parce et al. |
| 6,670,153 B2 | 12/2003 | Stern |
| 6,681,788 B2 | 1/2004 | Parce et al. |
| 6,685,810 B2 | 2/2004 | Noca et al. |
| 6,706,473 B1 | 3/2004 | Edman et al. |
| 6,707,548 B2 | 3/2004 | Kreimer et al. |
| 6,744,038 B2 | 6/2004 | Wang et al. |
| 6,749,734 B1 | 6/2004 | Simpson et al. |
| 6,767,706 B2 | 7/2004 | Quake et al. |
| 6,778,724 B2 | 8/2004 | Wang et al. |
| 6,779,559 B2 | 8/2004 | Parce et al. |
| 6,783,647 B2 | 8/2004 | Culbertson et al. |
| 6,784,420 B2 | 8/2004 | Wang et al. |
| 6,811,668 B1 | 11/2004 | Berndt et al. |
| 6,811,977 B2 | 11/2004 | Wold et al. |
| 6,814,859 B2 | 11/2004 | Koehler et al. |
| 6,815,664 B2 | 11/2004 | Wang et al. |
| 6,815,671 B2 | 11/2004 | Johnston et al. |
| 6,821,771 B2 | 11/2004 | Festoc |
| 6,830,936 B2 | 12/2004 | Anderson et al. |
| 6,833,068 B2 | 12/2004 | Paul et al. |
| 6,833,542 B2 | 12/2004 | Wang et al. |
| 6,848,462 B2 | 2/2005 | Covington et al. |
| 6,849,411 B2 | 2/2005 | Knapp et al. |
| 6,866,759 B2 | 3/2005 | Miles et al. |
| 6,875,403 B2 | 4/2005 | Liu et al. |
| 6,878,255 B1 | 4/2005 | Wang et al. |
| 6,884,395 B2 | 4/2005 | Tooke et al. |
| 6,900,021 B1 | 5/2005 | Harrison et al. |
| 6,913,697 B2 | 7/2005 | Lopez et al. |
| 6,915,679 B2 | 7/2005 | Chien et al. |
| 6,939,451 B2 | 9/2005 | Zhao et al. |
| 6,951,632 B2 | 10/2005 | Unger et al. |
| 6,953,676 B1 | 10/2005 | Wilding et al. |
| 6,958,119 B2 | 10/2005 | Yin et al. |
| 6,960,437 B2 | 11/2005 | Enzelberger et al. |
| 6,994,826 B1 | 2/2006 | Hasselbrink, Jr. et al. |
| 7,007,710 B2 | 3/2006 | Heller et al. |
| 7,010,391 B2 | 3/2006 | Handique et al. |
| 7,026,414 B2 | 4/2006 | Barron et al. |
| 7,037,417 B2 | 5/2006 | Rossier et al. |
| 7,041,481 B2 | 5/2006 | Anderson et al. |
| 7,041,509 B2 | 5/2006 | Parce et al. |
| 7,049,579 B2 | 5/2006 | Ozkan et al. |
| 7,060,224 B2 | 6/2006 | Edman et al. |
| 7,068,874 B2 | 6/2006 | Wang et al. |
| 7,070,681 B2 | 7/2006 | Santiago et al. |

(56) References Cited

U.S. PATENT DOCUMENTS

| | | |
|---|---|---|
| 7,081,622 B2 | 7/2006 | Kameoka et al. |
| 7,105,300 B2 | 9/2006 | Parce et al. |
| 7,105,810 B2 | 9/2006 | Kameoka et al. |
| 7,105,812 B2 | 9/2006 | Zhao et al. |
| 7,111,466 B2 | 9/2006 | Yamashita et al. |
| 7,138,062 B2 | 11/2006 | Yin et al. |
| 7,142,738 B2 | 11/2006 | Lee |
| 7,153,421 B2 | 12/2006 | Koehler et al. |
| 7,153,673 B2 | 12/2006 | Stern |
| 7,155,344 B1 | 12/2006 | Parce et al. |
| 7,156,969 B2 | 1/2007 | Mehta et al. |
| 7,160,423 B2 | 1/2007 | Chien et al. |
| 7,169,601 B1 | 1/2007 | Northrup et al. |
| 7,171,983 B2 | 2/2007 | Chien et al. |
| 7,179,423 B2 | 2/2007 | Bohm et al. |
| 7,198,701 B2 | 4/2007 | Ueda et al. |
| 7,211,184 B2 | 5/2007 | Webster et al. |
| 7,211,442 B2 | 5/2007 | Gilbert et al. |
| 7,214,299 B2 | 5/2007 | Armstrong |
| 7,217,542 B2 | 5/2007 | Tyvoll et al. |
| 7,231,819 B2 | 6/2007 | Jones et al. |
| 7,238,323 B2 | 7/2007 | Knapp et al. |
| 7,238,477 B2 | 7/2007 | Su et al. |
| 7,259,965 B2 | 8/2007 | Chang et al. |
| 7,297,324 B2 | 11/2007 | Tegrotenhuis et al. |
| 7,332,126 B2 | 2/2008 | Tooke et al. |
| 7,343,248 B2 | 3/2008 | Parce et al. |
| 7,344,681 B1 | 3/2008 | Fiechtner et al. |
| 7,371,533 B2 | 5/2008 | Slater et al. |
| 7,381,317 B2 | 6/2008 | Liu et al. |
| 7,391,020 B2 | 6/2008 | Bousse et al. |
| 7,399,396 B2 | 7/2008 | Barron et al. |
| 7,419,575 B2 | 9/2008 | Culbertson et al. |
| 7,425,700 B2 | 9/2008 | Stults et al. |
| 7,449,096 B2 | 11/2008 | Berndt et al. |
| 7,452,713 B2 | 11/2008 | Barlocchi et al. |
| 7,485,454 B1 | 2/2009 | Jury et al. |
| 7,521,186 B2 | 4/2009 | Burd Mehta |
| 7,531,073 B2 | 5/2009 | Barron et al. |
| 7,534,623 B2 | 5/2009 | Landers et al. |
| 7,537,807 B2 | 5/2009 | Craighead et al. |
| 7,544,019 B2 | 6/2009 | Vikner et al. |
| 7,547,510 B2 | 6/2009 | Daniel et al. |
| 7,591,883 B2 | 9/2009 | Kameoka et al. |
| 7,635,454 B2 | 12/2009 | Mastromatteo et al. |
| 7,641,860 B2 | 1/2010 | Matteo |
| 7,659,056 B1 | 2/2010 | De Vos |
| 7,744,762 B2 | 6/2010 | Lazar |
| 7,745,207 B2 | 6/2010 | Jovanovich et al. |
| 7,745,221 B2 | 6/2010 | Butler et al. |
| 7,749,365 B2 | 7/2010 | Nguyen et al. |
| 7,749,737 B2 | 7/2010 | McBride et al. |
| 7,752,895 B2 | 7/2010 | Lesieur |
| 7,784,330 B2 | 8/2010 | Angelescu et al. |
| RE41,762 E | 9/2010 | Lopez et al. |
| RE41,780 E | 9/2010 | Anderson et al. |
| 7,790,124 B2 | 9/2010 | Matted |
| 7,797,988 B2 | 9/2010 | Schultz et al. |
| 7,828,954 B2 | 11/2010 | Swanson |
| 7,829,025 B2 | 11/2010 | Ganesan et al. |
| 7,833,709 B2 | 11/2010 | Joseph et al. |
| 7,846,315 B2 | 12/2010 | Amirkhanian et al. |
| 7,851,185 B2 | 12/2010 | Dale et al. |
| 7,854,902 B2 | 12/2010 | Matteo |
| 7,867,193 B2 | 1/2011 | McKenna et al. |
| 7,867,194 B2 | 1/2011 | Fiering et al. |
| 7,892,819 B2 | 2/2011 | Wilding et al. |
| RE42,249 E | 3/2011 | Lopez et al. |
| 7,906,758 B2 | 3/2011 | Stults et al. |
| 7,915,030 B2 | 3/2011 | Inoue et al. |
| RE42,315 E | 5/2011 | Lopez et al. |
| 7,987,022 B2 | 7/2011 | Handique et al. |
| 7,998,418 B1 | 8/2011 | Matteo |
| 8,006,554 B2 | 8/2011 | Thorne, IV |
| 8,007,267 B2 | 8/2011 | Gao et al. |
| 8,021,614 B2 | 9/2011 | Huang et al. |
| 8,043,581 B2 | 10/2011 | Ganesan |
| 8,048,623 B1 | 11/2011 | Rublee et al. |
| 9,322,054 B2 * | 4/2016 | Egan .................. C12Q 1/6844 |
| 2001/0046701 A1 | 11/2001 | Schulte et al. |
| 2002/0012971 A1 | 1/2002 | Mehta |
| 2002/0060156 A1 | 5/2002 | Mathies et al. |
| 2002/0068357 A1 | 6/2002 | Mathies et al. |
| 2002/0123050 A1 | 9/2002 | Poponin |
| 2002/0123133 A1 | 9/2002 | Mehta et al. |
| 2002/0132265 A1 | 9/2002 | Kopf-Sill |
| 2002/0168671 A1 | 11/2002 | Burns et al. |
| 2002/0172969 A1 | 11/2002 | Burns et al. |
| 2002/0187560 A1 | 12/2002 | Pezzuto et al. |
| 2003/0000835 A1 | 1/2003 | Witt et al. |
| 2003/0003499 A1 | 1/2003 | Besemer et al. |
| 2003/0008308 A1 | 1/2003 | Enzelberger et al. |
| 2003/0038248 A1 | 2/2003 | Maher et al. |
| 2003/0104430 A1 | 6/2003 | Nerenberg et al. |
| 2003/0224436 A1 | 12/2003 | Nelson et al. |
| 2004/0014117 A1 | 1/2004 | Slepnev |
| 2004/0018530 A1 | 1/2004 | Bowser et al. |
| 2004/0043479 A1 | 3/2004 | Briscoe et al. |
| 2004/0053290 A1 | 3/2004 | Terbrueggen et al. |
| 2004/0081583 A1 | 4/2004 | Berndt et al. |
| 2004/0106130 A1 | 6/2004 | Besemer et al. |
| 2004/0115794 A1 | 6/2004 | Brubaker |
| 2004/0131504 A1 | 7/2004 | Landers et al. |
| 2004/0166525 A1 | 8/2004 | Besemer et al. |
| 2004/0171054 A1 | 9/2004 | Besemer et al. |
| 2004/0224325 A1 | 11/2004 | Knapp et al. |
| 2004/0245445 A1 | 12/2004 | Suzuki |
| 2004/0259100 A1 | 12/2004 | Gunderson et al. |
| 2004/0259106 A1 | 12/2004 | Gunderson et al. |
| 2005/0003421 A1 | 1/2005 | Besemer et al. |
| 2005/0032072 A1 | 2/2005 | Kautzer et al. |
| 2005/0042628 A1 | 2/2005 | Rava et al. |
| 2005/0053944 A1 | 3/2005 | Fuchs et al. |
| 2005/0053952 A1 | 3/2005 | Hong et al. |
| 2005/0084424 A1 | 4/2005 | Ganesan et al. |
| 2005/0084895 A1 | 4/2005 | Besemer et al. |
| 2005/0089953 A1 | 4/2005 | Besemer et al. |
| 2005/0106615 A1 | 4/2005 | Besemer et al. |
| 2005/0106617 A1 | 5/2005 | Besemer et al. |
| 2005/0106618 A1 | 5/2005 | Besemer et al. |
| 2005/0130213 A1 | 6/2005 | Morrison |
| 2005/0170362 A1 | 8/2005 | Wada et al. |
| 2005/0181403 A1 | 8/2005 | Rava et al. |
| 2005/0196779 A1 | 9/2005 | Ho et al. |
| 2005/0202504 A1 | 9/2005 | Anderson et al. |
| 2005/0208646 A1 | 9/2005 | Besemer et al. |
| 2005/0244933 A1 | 11/2005 | Panda et al. |
| 2005/0287572 A1 | 12/2005 | Mathies et al. |
| 2005/0287661 A1 | 12/2005 | Landers |
| 2006/0019274 A1 | 1/2006 | Goel |
| 2006/0040380 A1 | 2/2006 | Besemer et al. |
| 2006/0057029 A1 | 3/2006 | Coassin et al. |
| 2006/0073484 A1 | 4/2006 | Mathies et al. |
| 2006/0147912 A1 | 7/2006 | Corbett et al. |
| 2006/0166223 A1 | 7/2006 | Reed et al. |
| 2006/0166243 A1 | 7/2006 | Su et al. |
| 2006/0177844 A1 | 8/2006 | Ching et al. |
| 2006/0194306 A1 | 8/2006 | Herr et al. |
| 2006/0228717 A1 | 10/2006 | Joyce |
| 2006/0246493 A1 | 11/2006 | Jensen et al. |
| 2006/0246501 A1 | 11/2006 | Northrup |
| 2006/0260941 A1 | 11/2006 | Tan et al. |
| 2007/0026421 A1 | 2/2007 | Sundberg et al. |
| 2007/0042396 A1 | 2/2007 | Park et al. |
| 2007/0099211 A1 | 5/2007 | Aivazachvili et al. |
| 2007/0099288 A1 | 5/2007 | Gao et al. |
| 2007/0111303 A1 | 5/2007 | Inoue et al. |
| 2007/0117092 A1 | 5/2007 | Sadarangani et al. |
| 2007/0154895 A1 | 7/2007 | Spaid et al. |
| 2007/0175768 A1 | 8/2007 | Lau et al. |
| 2007/0184456 A1 | 8/2007 | Chee et al. |
| 2007/0196912 A1 | 8/2007 | Facer et al. |
| 2007/0231799 A1 | 10/2007 | Knight et al. |
| 2007/0238112 A1 | 10/2007 | Sohn et al. |

(56) References Cited

U.S. PATENT DOCUMENTS

| | | |
|---|---|---|
| 2007/0243109 A1 | 10/2007 | Chen et al. |
| 2007/0248958 A1 | 10/2007 | Jovanovich et al. |
| 2007/0292941 A1 | 10/2007 | Handique et al. |
| 2007/0298429 A1 | 12/2007 | Gumbrecht et al. |
| 2008/0003588 A1 | 1/2008 | Hasson et al. |
| 2008/0014576 A1 | 1/2008 | Jovanovich et al. |
| 2008/0038713 A1 | 2/2008 | Gao et al. |
| 2008/0038714 A1 | 2/2008 | Gao et al. |
| 2008/0050804 A1 | 2/2008 | Handique et al. |
| 2008/0108122 A1 | 5/2008 | Paul et al. |
| 2008/0124716 A1 | 5/2008 | Conney et al. |
| 2008/0160525 A1 | 7/2008 | Brown et al. |
| 2008/0160602 A1 | 7/2008 | He et al. |
| 2008/0164155 A1 | 7/2008 | Pease et al. |
| 2008/0166727 A1 | 7/2008 | Esfandyarpour et al. |
| 2008/0171325 A1 | 7/2008 | Brown et al. |
| 2008/0171382 A1 | 7/2008 | Brown et al. |
| 2008/0176230 A1 | 7/2008 | Owen et al. |
| 2008/0176289 A1 | 7/2008 | Zeng et al. |
| 2008/0176757 A1 | 7/2008 | Hassibi et al. |
| 2008/0179555 A1 | 7/2008 | Landers et al. |
| 2008/0182301 A1 | 7/2008 | Handique et al. |
| 2008/0193961 A1 | 8/2008 | Easley et al. |
| 2008/0206758 A1 | 8/2008 | Loge |
| 2008/0213770 A1 | 9/2008 | Williams et al. |
| 2008/0219890 A1 | 9/2008 | Lawson et al. |
| 2008/0241841 A1 | 10/2008 | Murakawa et al. |
| 2008/0241844 A1 | 10/2008 | Kellogg |
| 2008/0277387 A1 | 11/2008 | Landers et al. |
| 2008/0277595 A1 | 11/2008 | Lundquist et al. |
| 2008/0280285 A1 | 11/2008 | Chen et al. |
| 2009/0005259 A1 | 1/2009 | Drmanac |
| 2009/0011416 A1 | 1/2009 | Drmanac |
| 2009/0020427 A1 | 1/2009 | Tan et al. |
| 2009/0023603 A1 | 1/2009 | Selden et al. |
| 2009/0035770 A1 | 2/2009 | Mathies et al. |
| 2009/0036316 A1 | 2/2009 | Drmanac |
| 2009/0042241 A1 | 2/2009 | Yu-Chong et al. |
| 2009/0047713 A1 | 2/2009 | Handique |
| 2009/0053726 A1 | 2/2009 | Owen et al. |
| 2009/0059222 A1 | 3/2009 | Tan et al. |
| 2009/0061489 A1 | 3/2009 | Hanagata et al. |
| 2009/0082552 A1 | 3/2009 | Bynum et al. |
| 2009/0087884 A1 | 4/2009 | Beerling et al. |
| 2009/0092989 A1 | 4/2009 | Chang et al. |
| 2009/0111115 A1 | 4/2009 | Drmanac et al. |
| 2009/0130658 A1 | 5/2009 | Barlag et al. |
| 2009/0130719 A1 | 5/2009 | Handique |
| 2009/0148910 A1 | 6/2009 | Korampally et al. |
| 2009/0170092 A1 | 7/2009 | Landers et al. |
| 2009/0186344 A1 | 7/2009 | Farinas |
| 2009/0211908 A1 | 8/2009 | Farinas |
| 2009/0220984 A1 | 9/2009 | Dinges |
| 2009/0222212 A1 | 9/2009 | Curran |
| 2009/0229983 A1 | 9/2009 | Tan et al. |
| 2009/0255601 A1 | 10/2009 | Baeuerle et al. |
| 2009/0258415 A1 | 10/2009 | Bryning et al. |
| 2009/0275034 A1 | 11/2009 | Kiani et al. |
| 2009/0286245 A1 | 11/2009 | Bjornson et al. |
| 2009/0291435 A1 | 11/2009 | Unger et al. |
| 2009/0294287 A1 | 12/2009 | Morita et al. |
| 2009/0317806 A1 | 12/2009 | Hasson |
| 2009/0317824 A1 | 12/2009 | Woudenberg et al. |
| 2009/0317874 A1 | 12/2009 | Dale et al. |
| 2010/0021910 A1 | 1/2010 | Cao et al. |
| 2010/0028980 A1 | 2/2010 | Hasson et al. |
| 2010/0029915 A1 | 2/2010 | Duthie et al. |
| 2010/0032582 A1 | 2/2010 | Xia et al. |
| 2010/0055766 A1 | 3/2010 | Hwang et al. |
| 2010/0068765 A1 | 3/2010 | Zeng et al. |
| 2010/0086925 A1 | 4/2010 | Lee et al. |
| 2010/0086991 A1 | 4/2010 | Fish |
| 2010/0105040 A1 | 4/2010 | Lau et al. |
| 2010/0112645 A1 | 5/2010 | Clark et al. |
| 2010/0120129 A1 | 5/2010 | Amshey et al. |
| 2010/0129896 A1 | 5/2010 | Knapp et al. |
| 2010/0152066 A1 | 6/2010 | Malik et al. |
| 2010/0159576 A1 | 6/2010 | Song et al. |
| 2010/0167288 A1 | 7/2010 | Gale et al. |
| 2010/0167299 A1 | 7/2010 | Korlach |
| 2010/0173310 A1 | 7/2010 | Bousse et al. |
| 2010/0184020 A1 | 7/2010 | Beer |
| 2010/0233675 A1 | 9/2010 | Barrault et al. |
| 2010/0240044 A1 | 9/2010 | Kumar et al. |
| 2010/0243916 A1 | 9/2010 | Maurer et al. |
| 2010/0267013 A1 | 10/2010 | Su et al. |
| 2010/0267585 A1 | 10/2010 | Terbrueggen |
| 2010/0285578 A1 | 11/2010 | Selden et al. |
| 2010/0291666 A1 | 11/2010 | Collier et al. |
| 2010/0303687 A1 | 12/2010 | Blaga et al. |
| 2010/0307921 A1 | 12/2010 | Frazier |
| 2010/0311060 A1 | 12/2010 | Facer et al. |
| 2010/0323912 A1 | 12/2010 | Korlach et al. |
| 2010/0331194 A1 | 12/2010 | Turner et al. |
| 2011/0005932 A1 | 1/2011 | Jovanovich et al. |
| 2011/0014605 A1 | 1/2011 | Stone |
| 2011/0020920 A1 | 1/2011 | Mathies et al. |
| 2011/0027873 A1 | 2/2011 | Cho et al. |
| 2011/0033854 A1 | 2/2011 | Drmanac et al. |
| 2011/0039303 A1 | 2/2011 | Jovanovich et al. |
| 2011/0045503 A1 | 2/2011 | Gee et al. |
| 2012/0090996 A1* | 4/2012 | Trost .................. G01N 21/645 204/452 |
| 2012/0107912 A1 | 5/2012 | Hwang et al. |
| 2012/0115738 A1* | 5/2012 | Zhou .................... B01F 5/0683 506/9 |

FOREIGN PATENT DOCUMENTS

| | | |
|---|---|---|
| EP | 0 903 638 A1 | 3/1999 |
| EP | 1 584 692 A2 | 10/2005 |
| EP | 1 769 848 A2 | 4/2007 |
| JP | A-63-234145 | 9/1988 |
| JP | A-3-21337 | 1/1991 |
| WO | WO 94/05414 A1 | 3/1994 |
| WO | WO 96/03206 A1 | 2/1996 |
| WO | WO 96/04547 A1 | 2/1996 |
| WO | WO 96/12541 A1 | 5/1996 |
| WO | WO 96/30113 A1 | 10/1996 |
| WO | WO 97/02357 A1 | 1/1997 |
| WO | WO 97/012665 A1 | 4/1997 |
| WO | WO 97/16239 A1 | 5/1997 |
| WO | WO 97/28894 A1 | 8/1997 |
| WO | WO 97/38300 A1 | 10/1997 |
| WO | WO 98/54568 A1 | 12/1998 |
| WO | WO 99/09042 A2 | 2/1999 |
| WO | WO 99/46591 A2 | 9/1999 |
| WO | WO 99/61894 A1 | 12/1999 |
| WO | WO 99/64620 A2 | 12/1999 |
| WO | WO 00/10015 A1 | 2/2000 |
| WO | WO 00/45172 A1 | 8/2000 |
| WO | WO 01/06370 A1 | 1/2001 |
| WO | WO 02/38809 A1 | 5/2002 |
| WO | WO 03/042410 A1 | 5/2003 |
| WO | WO 2004/011149 A1 | 2/2004 |
| WO | WO 2005/094981 A1 | 10/2005 |
| WO | WO 2005/121963 A2 | 12/2005 |
| WO | WO 2008/005248 A2 | 1/2008 |
| WO | WO 2008/055257 A2 | 5/2008 |
| WO | WO 2008/055257 A3 | 5/2008 |
| WO | WO 2008/101196 A1 | 8/2008 |
| WO | WO 2008/143646 A2 | 11/2008 |
| WO | WO 2010/041088 A1 | 4/2010 |
| WO | WO 2010/141131 A1 | 12/2010 |
| WO | WO 2010/141139 A1 | 12/2010 |

OTHER PUBLICATIONS

Jun. 30, 2010 Written Opinion of the International Searching Authority issued in International Application No. PCT/US2010/026791.

Jan. 31, 2012 International Search Report issued in International Application No. PCT/US2011/056357.

(56) References Cited

OTHER PUBLICATIONS

Jan. 31, 2012 Written Opinion of the International Searching Authority issued in International Application No. PCT/US2011/056357.
Jun. 30, 2010 International Search Report issued in International Application No. PCT/US2010/025904.
Jun. 30, 2010 Written Opinion of the International Searching Authority issued in International Application No. PCT/US2010/025904.
Jun. 30, 2010 International Search Report issued in International Application No. PCT/US2010/026801.
Jun. 30, 2010 Written Opinion of the International Searching Authority issued in International Application No. PCT/US2010/026801.
Karlinsey et al., "AOFT-Based Multicolor Fluorescence Detection for Short Tandem Repeat (STR) Analysis in an Electrophoretic Microdevice", Journal of Royal Society of Chemistry 2008, Lab Chip, 2008, 8, 1285-1291.
Phillips, "Analysis of Single-cell cultures by immunoaffinity capillary electrophoresis with laser-induced fluorescence detection", Luminescence 2001, vol. 16, pp. 145-152.
Malcik et al., "The performance of a microchip-based fiber optic detection technique for the determination of $Ca^{2+}$ ions in urine", Science Direct, 2005, B 107, pp. 24-31.
Bellon et al., "Feasibility and Performances of a New, Multiplexed, Fast and Low-Cost Fiber-Optic NIR Spectrometer for the on-Line Measurement of Sugar in Fruits", Applied Spectroscopy, Jul. 1993, vol. 47, No. 7, pp. 1079-1083.
Daegupta et al., "Electroosmosis: A Reliable Fluid Propulsion System for Flow Injection Analysis", Anal. Chem. 1994, vol. 66, pp. 1792-1798.
Manz et al., "Miniaturized Total Chemical Analysis Systems: a Novel Concept for Chemical Sensing", Sensors and Actuators, 1990, vol. B1, pp. 244-248.
Jacobson et al, "Effects of Injection Schemes and Column Geometry on the Performance of Microchip Electrophoresis Devices", Anal. Chem., Apr. 1, 1994, vol. 66, No. 7, pp. 1107-1113.
Sandoval, "Method for the Accelerated Measurement of Elecroosmosis in Chemically Modified Tubes for Capillary Electrophoresis", Anal. Chem., Sep. 1, 1996, vol. 68, No. 17, pp. 2771-2775.
Chien et al., "Multiport Flow-Control System for Lab-on-a-Chip Microfluidic Devices", Anal. Chem., 2001, pp. 106-111.
Galambos et al., "An Optical Micro-Fluidic Viscometer", Micro-EL ctr.—MechanIcical System (MEMS), Nov. 15-20, 1998, DSC—vol. 66, pp. 187-191.
U.S. Appl. No. 13/064,094, filed Mar. 4, 2011.
U.S. Appl. No. 13/064,091, filed Mar. 4, 2011.
U.S. Appl. No. 13/064,093, filed Mar. 4, 2011.
U.S. Appl. No. 13/273,947, filed Oct. 14, 2011.
International Search Report and Written Opinion of the International Searching Authority issued Sep. 10, 2013, in PCT/US2013/027341, filed Feb. 22, 2013.
Australian Patent Examination Report No. 1 issued Nov. 11, 2014 in Patent Application No. 2013222269.

\* cited by examiner

MICROFLUIDIC CARTRIDGE

CROSS-REFERENCE TO RELATED APPLICATION

This application is a divisional application of U.S. patent application Ser. No. 13/773,350, filed Feb. 21, 2013, which claims the benefit of U.S. Provisional Application No. 61/601,937, filed Feb. 22, 2012. The entire disclosures of the prior applications are incorporated herein by reference in their entirety.

BACKGROUND

Genetic testing is used for various purposes, including forensic/identity testing, paternity testing, diagnostic testing, disease screening, environmental monitoring, food safety etc. Genetic testing relies on being able to analyze nucleic acids in a biological sample. Accordingly, improvements in nucleic acid analysis will further enhance the utility of genetic testing. In human identification-applications of genetic testing, such as forensic applications, nucleic acid analysis can be used to provide near certain matching of a biological sample to a person.

SUMMARY

In embodiments, a microfluidic cartridge can include at least one nucleic acid analysis portion. Each nucleic acid analysis portion can include a fluidic network being configured for micro-liter volumes or less, a sample input at the beginning of the fluidic network, a plurality of vent ports and fluidic channels in the fluidic network configured to effectuate hydrodynamic movement within the fluidic network, an extraction mixture reservoir in the fluidic network, a mixing chamber in the fluidic network, an amplification chamber in the fluidic network, and a separation channel in the fluidic network. The sample input can have a fitting that is configured to be mated to a complementary fitting of a sample acceptor to form a fluid-tight seal. The extraction mixture reservoir can be configured to hold an enzymatic mixture for performing nucleic acid extraction on a biological sample provided by the sample acceptor. The mixing chamber can be configured to mix amplification reagents and a portion of an extracted nucleic acid mixture. The amplification chamber can be configured to hold an amplification mixture during nucleic acid amplification. The separation channel can be configured to separate nucleic acid fragments.

In embodiments, a nucleic acid analyzer can include a microfluidic cartridge module configured to accept at least one microfluidic cartridge, a pressure module configured to be coupled to the plurality of vent ports to effectuate hydrodynamic movement within the fluidic network of the microfluidic cartridge, an extraction thermal module configured to impart temperatures to any of the microfluidic cartridge and a sample acceptor during nucleic acid extraction, an amplification thermal module configured to impart temperatures to the microfluidic cartridge during nucleic acid amplification, a high voltage module configured to apply high voltages on the microfluidic cartridge, a power module configured to provide operation powers to the nucleic acid analyzer, a detection module configured to detect labeled or dyed nucleic acids, and a controller module. The controller module can be configured to control the pressure module, the extraction thermal module, the amplification thermal module, the high voltage module, the power module, and the detection module according to a control procedure.

In embodiments, a method for performing nucleic acid analysis can include contacting an enzymatic mixture from an extraction mixture reservoir of a microfluidic cartridge with a biological sample collected with a sample acceptor to obtain an extracted nucleic acid mixture, mixing a portion of the extracted nucleic acid mixture with amplification reagents in a mixing chamber of the microfluidic cartridge to obtain an amplification mixture, amplifying template nucleic acid regions of nucleic acids in the amplification mixture in an amplification chamber of the microfluidic cartridge to obtain an amplified nucleic acid mixture, separating nucleic acid fragments in a portion of the amplified nucleic acid mixture in a separation channel of the microfluidic cartridge, and detecting the separated nucleic acid fragments within a detection region of the separation channel of the microfluidic cartridge to generate nucleic acid analysis data for subsequent processing by a nucleic acid analyzer.

BRIEF DESCRIPTION OF THE DRAWINGS

Various exemplary embodiments will be described in detail with reference to the following figures, wherein.

DETAILED DESCRIPTION OF THE EMBODIMENTS

Figure 1:
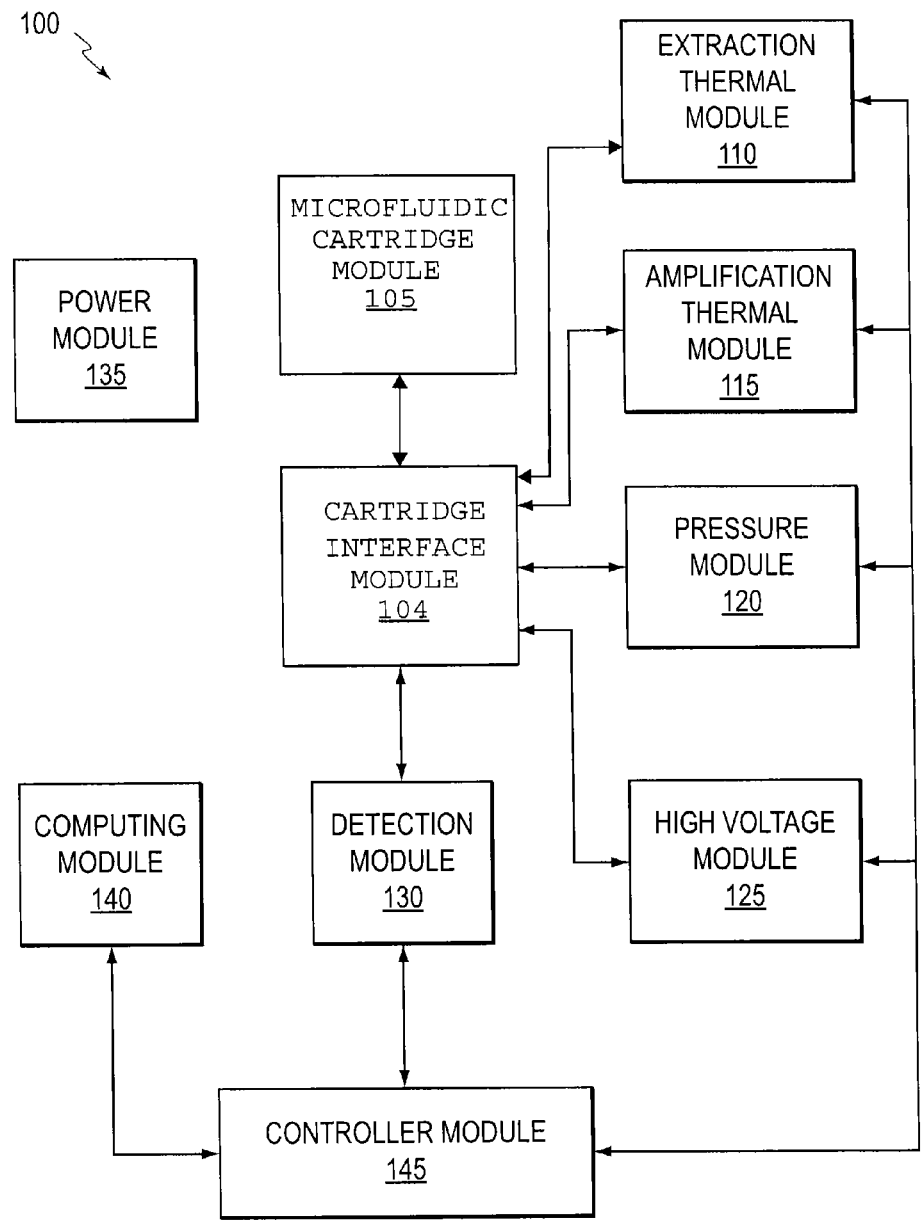
FIG. 1 shows a block diagram of an exemplary nucleic acid analyzer.

FIG. 1 shows a block diagram of an exemplary nucleic acid analyzer 100. As shown, the nucleic acid analyzer 100 can include a microfluidic cartridge module 105, a cartridge interface module 104, an extraction thermal module 110, an amplification thermal module 115, a pressure module 120, a high voltage module 125, a detection module 130, a power module 135, a computing module 140, and a controller module 145. The modules can be operably connected as shown in FIG. 1. In embodiments, the modules can also be combined or more than one of each module may be present in a nucleic acid analyzer.

The nucleic acid analyzer 100 is capable of performing nucleic acid analysis using a microfluidic cartridge. The nucleic acid analyzer 100 can be operated to perform nucleic acid analysis by a user without the need for substantial experience with and knowledge of the processes used to perform nucleic acid analysis. For example, the appropriate procedures for using the nucleic acid analyzer 100 can be learned in an hour or less. The nucleic acid analyzer 100 is designed to use liquid volumes on the order of micro-liters or less. By using micro-liter liquid volumes, nucleic analysis can be performed in reduced time as compared to time-intensive nucleic acid analysis currently in use. In embodiments, nucleic acid analysis can be performed in less than two hours.

The microfluidic cartridge module 105 is configured to accept one or more microfluidic cartridges (not shown). The cartridge interface module 104 is configured to operably couple the microfluidic cartridge module 105 to the other modules. In an embodiment, some of the other modules, such as the detection module 130, the extraction thermal module, the amplification thermal module 115, and the like, can be integrated in the cartridge interface module 104. The microfluidic cartridge can include a micro-to-macro interface and features that allow the microfluidic cartridge to be acted upon by other components of the nucleic acid analyzer 100. The microfluidic cartridge can be a disposable cartridge, such as a single-use cartridge. In general, microfluidic cartridges can include various features for performing any of nucleic acid extraction, nucleic acid amplification, and nucleic acid separation. Defined within the microfluidic cartridge is a fluidic network formed from fluidic channels, fluidic chambers and/or reservoirs, and other features for performing nucleic acid extraction, nucleic acid amplification, and/or nucleic acid separation. The microfluidic cartridge can be constructed from any suitable material. As examples, the microfluidic cartridge can be constructed from a plastic, polymeric material, glass, and the like. Additionally, the microfluidic cartridge can be constructed from multiple types of materials.

The extraction thermal module 110 is configured to impart suitable temperatures for nucleic acid extraction. The extraction thermal module 110 can be controlled by the controller module 145. The extraction thermal module 110 can be coupled to a cartridge or a sample acceptor during nucleic acid extraction. The extraction thermal module 110 can perform contact and/or non-contact thermal heating. In an example, the extraction thermal module 110 includes one or more contact heating units. Heating with the extraction thermal module can facilitate the extraction of nucleic acids with thermophilic enzymes.

The amplification thermal module 115 is configured to impart suitable temperatures to the microfluidic cartridge during nucleic acid amplification. The amplification thermal module 115 can be controlled by the controller module 145. In embodiments, the amplification thermal module 115 can be configured to impart thermal gradients and perform temperature sensing in a thermal cycling process in an amplification chamber of the microfluidic cartridge. The amplification thermal module 115 can perform contact and/or non-contact thermal heating. In an example, the amplification thermal module 115 includes a non-contact heating unit, such as an infrared light source. The infrared light source can be a halogen light bulb. Further, the amplification thermal module 115 can include a temperature sensing unit. In an embodiment, the temperature sensing unit is an infrared pyrometer that measures blackbody radiation to determine the temperature of a selected portion of the microfluidic cartridge. Further, in embodiments, a single thermal module can be configured to impart temperature changes for both extraction and amplification, as necessary, using the same heating means.

The pressure module 120 is operably coupled to the microfluidic cartridge by, for example, the micro-to-macro interface. The pressure module 120 can be controlled by the controller module 145. The pressure module 120 is configured to provide pressures and/or vacuums (i.e., positive and/or negative pressures) to the microfluidic cartridge to move fluid within a fluidic network of the microfluidic cartridge. In other words, the pressure module 120 can effectuate hydrodynamic movement using, for example, pneumatic pressure in the microfluidic cartridge. In an embodiment, the pressure module 120 is coupled to one or more clusters of vent ports on the microfluidic cartridge at the micro-to-macro interface. The pressure module 120 can connect a solenoid manifold to the plurality of vent ports of the microfluidic cartridge at the micro-to-macro interface. The pressure module 120 can impart pressure to each vent port independently to move fluid through the fluidic network in the microfluidic cartridge. In an embodiment, the microfluidic cartridge has one or more valves that are configured to be actuated by the pressure module 120. The pressure module 120 can include a pressure/vacuum system, such as a pneumatic pressure/vacuum system, to suitably control hydrodynamic movement in the fluidic network of the microfluidic cartridge.

The power module 135 generates various operation powers for various components of the nucleic acid analyzer 100. In an example, the nucleic acid analyzer 100 is implemented using a modular design. Each module of the nucleic acid analyzer 100 requires an operation power supply, which can be different from the other modules. The power module 135 can receive an AC power input, such as 100-240 V, 50-60 Hz, single phase AC power from a power outlet. The power module 135 can use the AC power input to generate 5 V, 12 V, 24 V, and the like, to provide operation powers for the various components of the nucleic acid analyzer 100. In other embodiments, the power module 135 can be a battery.

The power module 135 also imparts power to the high voltage module 125 as required for nucleic acid processes on the microfluidic cartridge, such as electrophoretic separation. The power module 135 can implement various protective functions, such as power outage protection, graceful shut-down, and the like, to protect the various components and data against power failure. In an embodiment, the power module 160 includes a back-up power, such as a battery module, to support one or more protective functions, such as graceful shut-down.

The high voltage module 125 receives power from the power module 160 and generates high voltages such as 1000 V, 2000 V, and the like, required for nucleic acid processes on the microfluidic cartridge, such as electrophoretic separation. The high voltage module 125 can apply the high voltages to the microfluidic cartridge under control of the controller module 145. For example, the high voltage module 140 includes an interface that applies the high voltages to electrodes on the microfluidic cartridge to induce electrokinetic injection and/or electrophoretic separation.

The detection module 130 includes components configured to detect labeled or dyed nucleic acids. The detection module 130 can be controlled by the controller module 145. In an embodiment, the detection module 130 is configured for fluorescence detection, such as multicolor fluorescence detection. The detection module 130 can include a laser source unit, an optical unit and a detector unit. The optical unit includes a set of optics. In an embodiment, the optical unit includes a self-calibrating array of confocal optical components. The laser source unit emits a laser beam. In an example, the laser source unit includes an argon-ion laser unit. In another example, the laser source unit includes a solid state laser, such as a coherent sapphire optically pumped semiconductor laser unit. The solid state laser has the advantages of reduced size, weight and power consumption.

In operation, the set of optics can direct the laser beam to penetrate a detection region of a separation channel in the microfluidic cartridge. The laser beam can excite fluorescent molecules attached to nucleic acids to emit fluorescence. The set of optics can then collect and direct the emitted fluorescence to the detector unit for detection. The detector unit can convert the detected fluorescence into data for subsequent processing by the computing module 140. An exemplary detection technique is disclosed by co-pending U.S. application Ser. No. 13/273,947 entitled, "Micro Fluidic Optic Design," which is hereby incorporated herein by reference in its entirety.

The computing module 140 includes computing and communication units. The computing module 140 is operably coupled to the controller module 180. The computing module 140 can provide a user interface. The user interface can provide the status of the nucleic acid analyzer 100 and can receive user instructions for controlling the operation of the nucleic acid analyzer 100. The computing module 140 includes various storage media to store software instructions and data. The computing module 140 can include nucleic analysis software that can perform data processing based on raw data obtained from the detection module 130. In addition, the computing module 140 can be coupled to external processing units, such as a database, a server, and the like to further process the data obtained from nucleic acid analysis.

The controller module 145 can receive status signals and feedback signals from the various components and provide control signals to the various components according to a nucleic acid analysis procedure. In addition, the controller module 145 can provide the status signals to the computing module 140 to inform a user of the status of nucleic acid analysis. Further, the controller module 145 can receive user instructions from the computing module 140 and can provide control signals to the various components based on user instructions.

Figure 2:
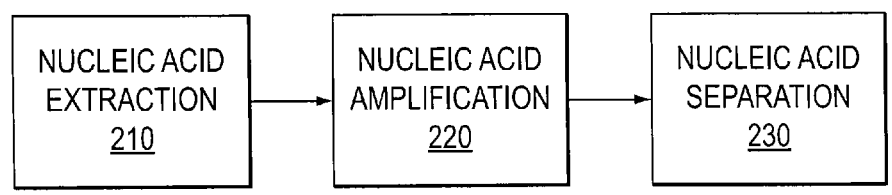
FIG. 2 shows a conceptual diagram of the functions performed by embodiments of the microfluidic cartridge.

FIG. 2 shows a conceptual diagram of the functions performed by embodiments of the microfluidic cartridge. The microfluidic cartridge includes various features for performing nucleic acid extraction 210, nucleic acid amplification 220, and/or nucleic acid separation 230. Nucleic acids include DNA and RNA. In an example, extraction, amplification, and separation are performed solely to analyze DNA. In another example, RNA is analyzed by, for example, extracting RNA, reverse transcribing RNA and amplifying the resulting cDNA, and separating the DNA. Importantly, in embodiments, no additional purification feature is required between features for performing nucleic acid extraction 210 and nucleic acid amplification 220.

Nucleic acid extraction 210 is performed on a biological sample. Examples of biological samples that contain nucleic acids include saliva, blood, fecal, and urine samples. To extract the nucleic acids from the biological sample, other components of the cell must be inactivated and/or degraded. Nucleic acid extraction 210 can be carried out by contacting the biological sample with an enzymatic mixture. The enzymatic mixture can be a liquid-phase mixture. The enzymatic mixture can enzymatically digest proteins and other cellular interferences in the biological sample, with the exception of nucleic acids. In an embodiment, the enzymatic mixture includes thermostable proteinases. The thermostable proteinases can be from thermophilic Bacillus species. For example, a liquid phase mixture including thermostable proteinases from thermophilic Bacillus species is disclosed in U.S. Patent Application Publication No. 2004/0197788, which is incorporated herein by reference in its entirety. In an embodiment, the enzymatic mixture performs nucleic acid extraction when a sample collection portion (e.g., in the form of a swab) of a sample acceptor holding a biological sample is contacted by the enzymatic mixture. In an example, a final nucleic acid concentration of the resulting extracted nucleic acid mixture is in a range of 0.5-20 ng/μL.

Nucleic acid extraction 210 can be followed by nucleic acid amplification 220 without additional treatment of the extracted nucleic acid mixture. Specifically, a portion of the extracted nucleic acid mixture can be mixed with amplification reagents to perform nucleic acid amplification 220 without additional purification steps. The enzymatic nucleic acid extraction procedure described herein can generate sufficiently clean nucleic acid solutions to proceed with amplification. The nucleic acid solutions may contain species that are sufficiently broken down so that they do not interfere with subsequent reactions.

Nucleic acid amplification 220 can follow nucleic acid extraction 210. Nucleic acid amplification 220 is performed on template nucleic acid regions (sequences) in an extracted nucleic acid mixture. Nucleic acid amplification 220 can be performed by polymerase chain reaction (PCR), among other amplification techniques. To perform PCR, DNA having one or more template regions is mixed with suitable PCR reagents. PCR reagents include a DNA polymerase, nucleotides, and primers (oligonucleotides) that contain sequences complementary to the template DNA sequences. The polymerase enzymatically produces a new DNA strand from the template DNA by using the template DNA to guide synthesis of the new DNA strand through the extension of the primers by incorporating nucleotides at the end of the primers. The primers can be tagged with labels to generate labeled synthesized DNA strands after amplification. In other embodiments, the synthesized DNA strands can be tagged with labels during PCR by, for example, using labeled nucleotides to synthesize the DNA strands. The labels can be fluorescent labels. Fluorescents labels emit fluorescence of known wavelengths when excited by a laser beam. PCR requires thermal cycling. Thermal cycling is the repeated heating and cooling of the PCR mixture, including the PCR reagents and template DNA. Thermal cycling is conducted to melt the DNA, hybridize the primers to the template DNA, and to perform enzymatic replication of the template DNA regions. As PCR progresses, the DNA generated is itself used as template DNA for replication in succeeding cycles. Thus, PCR is a chain reaction that exponentially amplifies the template DNA regions. Amplification results in an amplified nucleic acid mixture.

Nucleic acid separation 230 can follow nucleic acid amplification 220. Nucleic acid separation 230 is performed to separate nucleic acid fragments in a nucleic acid mixture, such as an amplified nucleic acid mixture, and can enable detection and analysis of the nucleic acid fragments. In embodiments, electrophoresis can be used to separate the nucleic acid fragments by size. In electrophoresis, nucleic acid fragments are subjected to an electric field to force the nucleic acid fragments through a sieving medium. The nucleic acid fragments migrate by force of the electric field at different speeds based on size. An electric field induces a nucleic acid fragment to migrate due to the net negative charge of the sugar-phosphate backbone of the nucleic acid fragment. The sieving medium can be a polymer matrix formed from a polymer solution. As examples for forming such a matrix, suitable polymer solutions are disclosed in U.S. Pat. Nos. 8,207,258, 8,017,682, 7,862,699, 7,531,073, 7,399,396, 7,371,533, 7,026,414, 6,811,977 and 6,455,682, which are incorporated herein by reference in their entireties. In an example, a sieving polymer matrix can be used to yield single-base resolution. During or after separation, the DNA fragments can be detected and analyzed.

Figure 3:
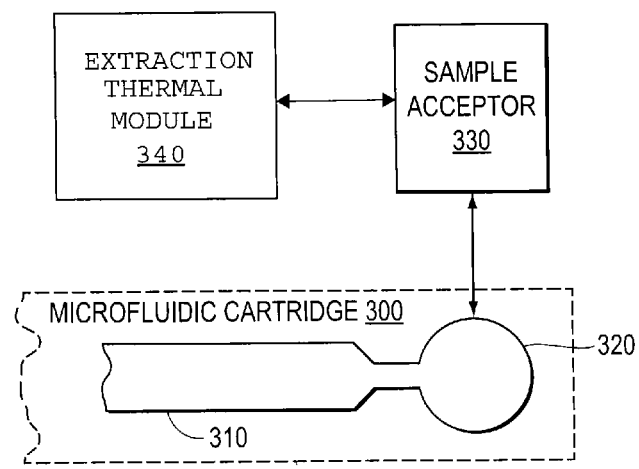
FIG. 3 shows exemplary features for performing nucleic acid extraction.

FIG. 3 shows exemplary features for performing nucleic acid extraction that can be included within a microfluidic cartridge 300. As shown, the microfluidic cartridge 300 can be provided with an extraction mixture reservoir 310 in fluid communication with a sample input 320. Other features for performing nucleic acid extraction may be provided off-cartridge. In an embodiment, the off-cartridge features include a sample acceptor 330 and an extraction thermal module 340. In an example, the sample acceptor 330 and the extraction thermal module 340 are coupled together. The extraction mixture reservoir 310 is configured to hold the enzymatic mixture for performing nucleic acid extraction. In embodiments, the extraction mixture reservoir is configured to hold from about 25 µl to about 500 µl, such as from about 200 µl to about 250 µl or about 225 µl, of the enzymatic mixture. The enzymatic mixture is provided to or pre-loaded in the extraction mixture reservoir 310.

In use, the sample acceptor 330 is coupled with the sample input 320 such that the extraction mixture reservoir 310, the sample input 320, and the sample acceptor 330 are in fluid communication. The sample acceptor 330 presents a previously-collected biological sample for nucleic acid extraction. In embodiments, the minimal amount of biological material required to be presented is about 100 cells. The enzymatic mixture can be provided from the extraction mixture reservoir 310 to the sample acceptor 330 in order to initiate nucleic acid extraction. To aid enzymatic digestion, the enzymatic mixture can be moved in a back-and-forth motion within the sample acceptor 330 and the extraction mixture reservoir 310. The extraction thermal module 340 can heat the enzymatic mixture to promote enzymatic digestion of cellular components other than nucleic acids. Extraction can be performed at a first temperature. Enzymes of the enzymatic mixture can be inactivated at a second higher temperature to conclude nucleic acid extraction. In an example, nucleic acid extraction is performed at 75° C. for 10 minutes to extract the nucleic acids through enzymatic digestion. Then, the heat is increased and held at 95° C. to inactivate the enzymes in the enzymatic mixture. In such an example, the enzymes include thermostable proteinases that functional at 75° C., but that are inactivated at higher temperatures, such as 95° C. Upon completion of enzymatic digestion, the resulting extracted nucleic acid mixture can be received by and stored in the extraction mixture reservoir 310 for further processing. The extraction mixture reservoir 310 can have one or more fluidic channels (not shown) branching from the extraction mixture reservoir 310 to provide the extracted nucleic acid mixture to other portions of the microfluidic cartridge through a fluidic network.

Figure 4:
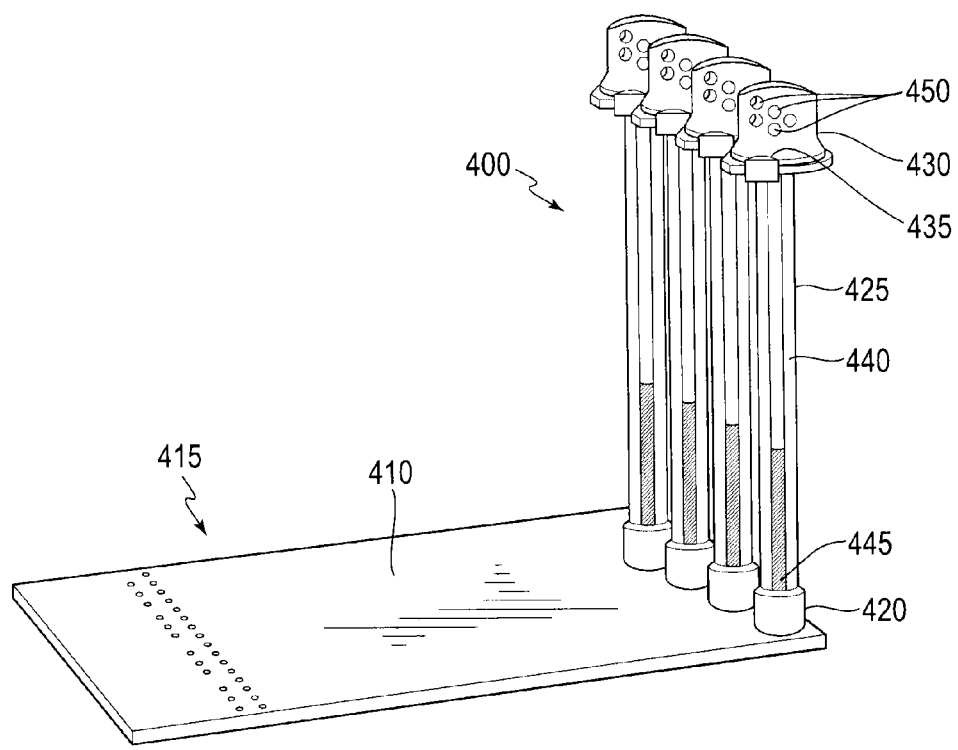
FIG. 4 shows a plurality of exemplary sample acceptors fluidically coupled to an exemplary microfluidic cartridge.
Figure 5:
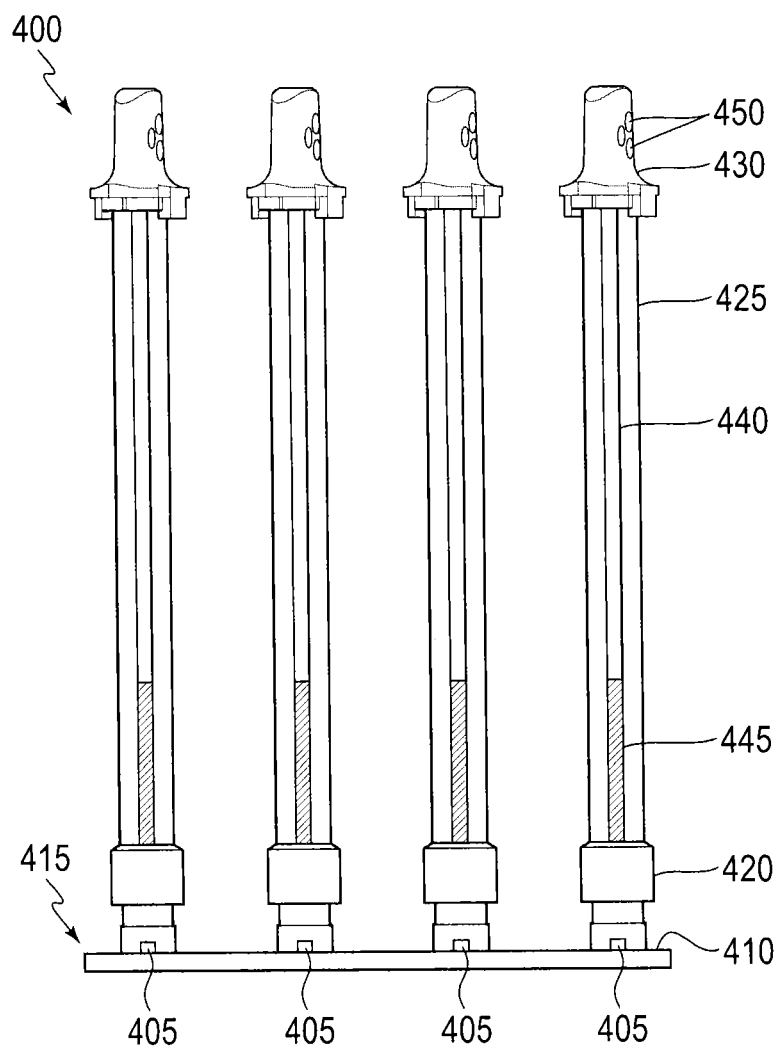
FIG. 5 shows another view of the plurality of exemplary sample acceptors fluidically coupled to the exemplary microfluidic cartridge shown in FIG. 4.

FIGS. 4 and 5 show a plurality of exemplary sample acceptors 400 fluidically coupled to a plurality of exemplary sample inputs 405 formed on an outer surface 410 of an exemplary microfluidic cartridge 415. As shown, each sample input 405 includes a portion surrounding an opening that protrudes from the outer surface 410 of the microfluidic cartridge 415. In FIGS. 4 and 5, four sample acceptors 400 are fluidically coupled to four sample inputs 405 of the microfluidic cartridge 415. In other embodiments, the microfluidic cartridge 415 can include less than four sample inputs 405, including a single sample input 405, or more than four sample inputs 405 for fluidically coupling the same number of sample acceptors 400. The sample inputs 405, as well as the sample acceptors 400, can be of the same of different types. As shown, the sample acceptors 400 and the sample inputs 405 are of the same type. Alternatively, one or more of the sample acceptors 400 and the sample inputs 405 can be of different types.

As further shown, each sample acceptor 400 includes an input-matable portion 420, an acceptor portion 425, and a detachable portion 430 for sample collection. The input-matable portion 420 is at one end of the acceptor portion 425. The acceptor portion 425 is in the form of a barrel similar to a syringe barrel. The input-matable portion 420 can be configured to be coupled to the sample input 405 to form a fluid-tight seal. The input-matable portion 420 and the sample input 405 can be based on any small-scale fluid fitting system. In embodiments, the input-matable portion 420 and the sample input 405 each have a universal connector selected from the group consisting of Luer-Lok connectors, threaded connectors, and flanged connectors. For example, the input-matable portion 420 and the sample input 405 can be based on a Luer-Lok fitting system. In an embodiment, the sample input 405 is threaded such as to be a female Luer-Lok fitting and the input-matable portion 420 is based on a complementary male Luer-Lok fitting that has an inner flange configured to fit inside the opening of the sample input 405 and a second outer flange that is threaded and configured to be screw-fitted onto the threaded sample input 405.

The detachable portion 430 is configured to be removed from the acceptor portion 425 to collect a biological sample and again coupled to the acceptor portion 425 after collection of the biological sample has been completed. To effectuate removable coupling, the detachable portion 430 includes a flanged grip 435. The flanged grip 435 can be configured to be reversibly coupled to a complementary end of the acceptor portion 425. Extending from the flanged grip 435 is an elongated member 440 that includes a sample collection portion 445. The sample collection portion 445 can be in the form of a swab.

Nucleic acid extraction can be performed when the microfluidic cartridge 415 is coupled to a pressure module of a nucleic acid analyzer. The pressure module can provide positive and/or negative pressure to force an enzymatic mixture from an extraction mixture reservoir of the microfluidic cartridge 415 into the sample acceptor 400 in order to perform nucleic acid extraction on a biological sample presented by the sample acceptor 400. To aid enzymatic digestion, the pressure module, through positive and/or negative pressure, can move the enzymatic mixture in a back-and-forth motion within the sample acceptor 400 and the extraction mixture reservoir of the microfluidic cartridge 415. The flanged grip 435 of the sample acceptor 400 can be gas permeable to permit gas (e.g., air) to exit the sample acceptor 400. As shown, the sample acceptor 400 is made gas permeable by including openings 450 defined in the flanged grip 435.

The microfluidic cartridge 415 can include a vent port in fluid communication with the extraction mixture reservoir, which can place the pressure module in serial fluid communication with the sample acceptor 400 through the extraction mixture reservoir and the sample input 405. In embodiments, the pressure module applies positive and/or negative pressure to the distal end of the extraction mixture reservoir to force a volume of the enzymatic mixture through the sample input 405 into the sample acceptor 400, where the enzymatic mixture can submerge the biological sample presented on the sample collection portion 445 of the sample acceptor 400. The pressure module, under control of a controller module, can then force the enzymatic mixture and dissolved biological sample back into the extraction mixture reservoir. The pressure module can revert at least a major portion of the enzymatic/biological sample mixture back into the sample acceptor 400. This back-and-forth motion can be continued by operation of the pressure module using positive and/or negative pressure, such as pneumatic pressure, and discontinued once nucleic acid extraction is completed. The turbidity associated with the back-and-forth motion can aid nucleic acid extraction and can produce a well-mixed solution of extracted nucleic acids.

During nucleic acid extraction, the sample acceptor 400 can be coupled to an extraction thermal module of a nucleic acid analyzer. As discussed above, the extraction thermal module can heat the enzymatic mixture to promote enzymatic digestion of cellular components (other than nucleic acids) of the biological sample presented by the sample acceptor 400.

Figure 6:
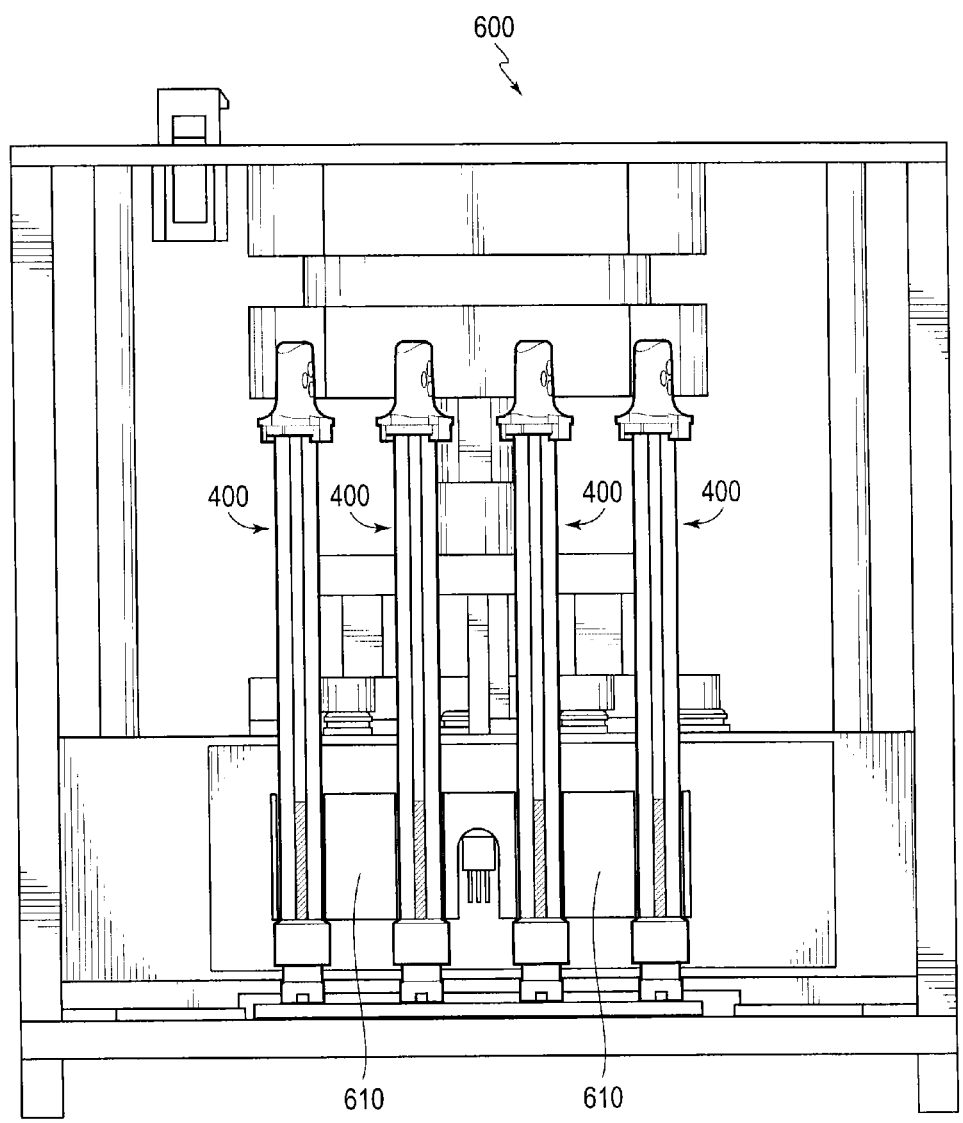
FIG. 6 shows a portion of an exemplary nucleic acid analyzer that includes an extraction thermal module.

FIG. 6 shows a portion of an exemplary nucleic acid analyzer 600 that includes an extraction thermal module 610. As shown, sample acceptors 400 are received by the nucleic acid analyzer 600 such that they are operably coupled to the extraction thermal module 610. The extraction thermal module 610 can heat the sample acceptors 400 by contact heating.

Figure 7:
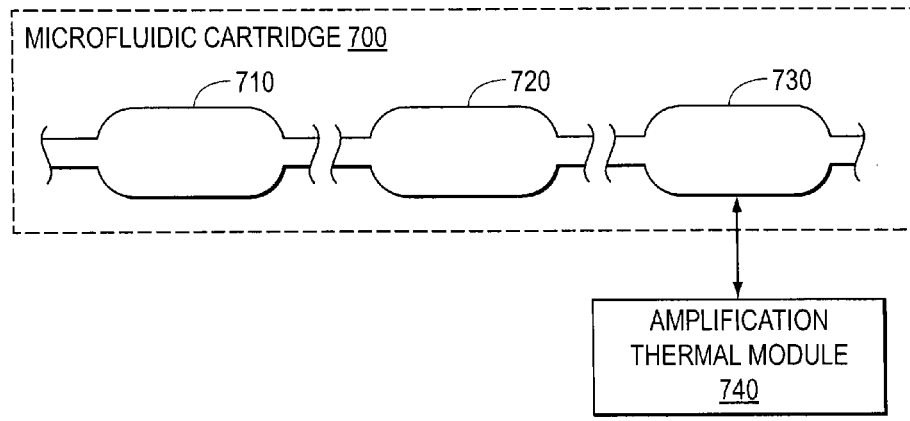
FIG. 7 shows exemplary features for performing nucleic acid amplification.

FIG. 7 shows exemplary features for performing nucleic acid amplification on template nucleic acid regions in an extracted nucleic acid mixture. As shown, on-cartridge features included within a microfluidic cartridge 700 include an amplification reagent reservoir 710, a mixing chamber 720, and an amplification chamber 730. In this example, the amplification reagent reservoir 710, the mixing chamber 720, and the amplification chamber 730 are in serial fluid communication. However, other types of fluid communication are possible. The amplification reagent reservoir 710 holds amplification reagents for performing a nucleic acid amplification reaction. In an embodiment, the amplification reagents are PCR reagents, including a DNA polymerase, nucleotides, and primers. The amplification reagents can be contained in more than one amplification reagent reservoir 710. In an embodiment, the DNA polymerase is contained in a separate amplification reagent reservoir 710 from the primers and nucleotides.

During operation, the amplification reagents are provided to the mixing chamber 720. A portion of an extracted nucleic acid mixture is also provided to the mixing chamber 720. In this embodiment, the extracted nucleic acid mixture portion is provided to the mixing chamber 720 using the same fluidic channel as used to provide the amplification reagents to the mixing chamber 720. In embodiments, the extracted nucleic acid mixture portion is from about 1 µl to about 50 µl, such as from about 25 µl to about 35 µl or about 30 µl. The extracted nucleic acid mixture portion can be mixed with the amplification reagents in a ratio of from 0.1:1 to 1:1 or from 1:1 to 1:0.1 depending on the concentrations of the reagents. The total volume of the extracted nucleic acid mixture portion and the amplification reagents can be from about 25 µl to about 100 µl. The extracted nucleic acid mixture portion and the amplification reagents can be prevented from mixing until they reach the mixing chamber 720 by moving the extracted nucleic acid mixture portion and the amplification reagents in discrete volumes. The discrete volumes can be physically separated. For instance, because the extracted nucleic acid mixture portion and the amplification reagents are in liquid volumes, the liquid volumes can be kept physically separate by moving another fluid, such as air, in between the liquid volumes. In an alternative embodiment, the extracted nucleic acid mixture portion can be provided to the mixing chamber using a different fluidic channel.

In the mixing chamber 720, the extracted nucleic acid mixture portion containing the extracted nucleic acids and the amplification reagents are mixed. The mixing chamber can hold a total solution volume greater than the total solution volume to be introduced. This design allows space for air bubbles to rise from the fluid surface to the top of the chamber and the contained gas (e.g., air) can escape through a fluidically-coupled vent. The dimensions of the mixing chamber 720 can be further optimized for the escape of bubbles. For example, the vent can be configured on the opposite end of an elongated, chamber from the input channels where fluid is introduced. The input channels in fluid communication with the mixing chamber 720 may be in a perpendicular orientation to the long side of the mixing chamber 720 so as to promote turbidity among the introduced fluids. In other words, the mixing chamber 720 can be configured to have a liquid mixing portion and a gas vent portion above the liquid mixing portion. The gas vent portion can be above each fluidic channel in communication with the mixing chamber 720. Each fluidic channel in communication with the mixing chamber 720 can interface with the mixing chamber 720 at the bottom portion of the mixing chamber 720 to prevent bubble development and generate a rising fluid level that pushes bubbles to the gas vent portion. In an embodiment, the mixing chamber 720 includes a hydrophobic surface that repels aqueous liquid away from the gas vent portion. Thus, the hydrophobic surface can protect against the extracted nucleic acid mixture portion or amplification reagents from entering or being retained in the gas vent portion. The hydrophobic surface can function as a barrier separating the liquid mixing portion and the gas vent portion. The hydrophobic surface can have non-uniform geometries, heights, levels, and/or areas on the mixing chamber surface. Alternatively, the hydrophobic surface can be uniform.

The extracted nucleic acid mixture portion and the amplification reagents are provided to and mixed in the liquid mixing portion of the mixing chamber 720 to obtain an amplification mixture. Using features discussed above, the mixing chamber 720 can be configured to disrupt the laminar flow of the extracted nucleic acid mixture portion and the amplification reagents as they enter the mixing chamber 720. Laminar flow disruption can cause mixing of the amplification reagents and the extracted nucleic acid mixture portion to obtain the amplification mixture. Gas, such as air, released during mixing of the extracted nucleic acid mixture portion and the amplification reagents can be released from the liquid mixing portion to the gas vent portion of the mixing chamber 720. From the gas vent portion, gas can be released from the microfluidic cartridge 700 though a channel in fluid communication with the mixing chamber 720. The fluidic channel for gas release can be a dedicated channel for this purpose or can be a non-exclusive channel that is used for other purposes. A gas vent outlet can be at the end of the fluidic channel to allow the gas to escape into the environment outside the microfluidic cartridge 700. By venting gas, the mixing chamber 720 can protect against bubbles being present in the amplification mixture during further processing of the sample. The mixing chamber 720 is in fluid communication with the amplification chamber 730.

The amplification chamber 730 is configured for nucleic acid amplification. In embodiments, the amplification chamber 730 is used to perform PCR. To perform PCR, the amplification chamber 730 can be configured for thermal cycling from an amplification thermal module 740. In an embodiment, the amplification thermal module 740 includes a heating unit configured to perform non-contact or contact heating. As an example, the heating unit is an infrared light source for non-contact heating. The amplification thermal module 740 can include a temperature sensing unit. In an embodiment, the temperature sensing unit is an infrared pyrometer. To improve pyrometer sensing accuracy, the amplification chamber 730 can include a thinner portion for infrared pyrometer measurements. The infrared pyrometer measurements at the thinner portion can more accurately reflect the temperature of liquid within the amplification chamber 730. Thermal cycling requires cooling. Thus, the amplification chamber 730 can be configured through material choice to perform rapid cooling when not being heated. In such embodiments, the amplification thermal module 740 does not need a cooling unit to cool the amplification chamber 730. Alternatively, the amplification thermal module 740 can include a cooling unit to perform cooling. As an example, the cooling unit is a cooling fan. In another embodiment, the cooling unit is a compressed air outlet.

During operation, the amplification mixture is provided to the amplification chamber 730. In embodiments, the amplification mixture provided to the amplification chamber 730 has a volume of from about 100 µl to about 5 µl, such as from about 500 µl to about 1.5 µl or about 1 µl. The amplification mixture can have laminar flow as it is provided to the amplification chamber 730 from a fluidic channel exiting the mixing chamber 720. In the amplification chamber 730, the amplification mixture is placed under reaction conditions to amplify template nucleic acid regions (sequences). As an example, the amplification mixture is thermal cycled to perform PCR. During amplification, the amplified nucleic acids can be tagged with labels, such as fluorescent labels. After amplification, the resulting amplified nucleic acid mixture is available for further processing.

Figure 8:
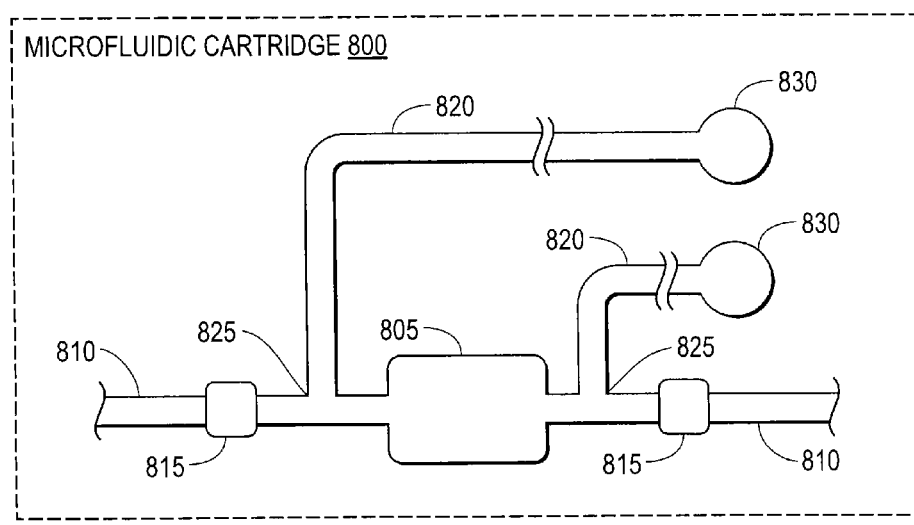
FIG. 8 shows exemplary features of a loadable reservoir.

FIG. 8 shows exemplary features of a loadable reservoir that can be included within a microfluidic cartridge 800. As shown, the microfluidic cartridge 800 includes a reagent reservoir 805 that can be loaded with a reagent solution for performing nucleic acid analysis. The reagent reservoir 805 can be configured to hold any of extraction, amplification, and separation reagents. For example, the reagent reservoir 805 is an amplification reagent reservoir as discussed above. The reagent reservoir 805 is in fluid communication with one or more fluidic channels 810 that lead to other portions of a fluidic network of the microfluidic cartridge 800. One or more (e.g., two) seals 815 are positioned in the one or more (e.g., two) fluidic channels 810 to block the reagent solution from entering or prematurely entering other portions of the fluidic network. The seals 815 can be non-reusable (one-time) or reusable seals and each seal 815 can be of a different type. In embodiments, the seals 815 are frangible seals that can be broken by pressure supplied from a pressure module of a nucleic acid analyzer. The seals 815 can be broken in order to move the reagent solution to another portion of the fluidic network of the microfluidic cartridge 800 and/or to bring the reagent solution under hydrodynamic control of a pressure module of a nucleic acid analyzer. The microfluidic cartridge 800 further includes one or more (e.g., two) bypass fluidic channels 820 in fluid communication with the reagent reservoir 805. The bypass fluidic channels 820 merge with the fluidic channels 810 at junctions 825. A port 830 is in fluid communication with each bypass channel 820 at the other end of the bypass channel 820. One of the ports 830 can be designated as a filling port and the other of the ports 830 can be designated as a gas outlet. At least the filling port 830 can be configured to be fluidically coupled to an off-cartridge store of the reagent solution to be loaded in the reagent reservoir 805.

The reagent reservoir 805 can be loaded with the reagent solution by providing the reagent solution to the reagent reservoir 805 through one of the ports 830 and the associated bypass fluidic channel 820. Gas (e.g., air) present in the reagent reservoir 805 (and the filling port 830 and the associated bypass channel 820) that is displaced during loading of the reagent solution can be expelled out of the reagent reservoir 805 through the other bypass fluidic channel 820 and the associated gas outlet port 830. The gas outlet port 830 can be open to the environment outside the microfluidic cartridge 800 during reagent loading to permit gas to be expelled from the microfluidic cartridge 800. After loading, a sealing member (not shown), such as an adhesive film, can be placed over the ports 830 to protect against contamination. The sealing member can be air-permeable, but not liquid-permeable. The sealing member can be hydrophobic. In embodiments, the sealing member is made from a pressure-sensitive adhesive (PSA) polymer.

Figure 9:
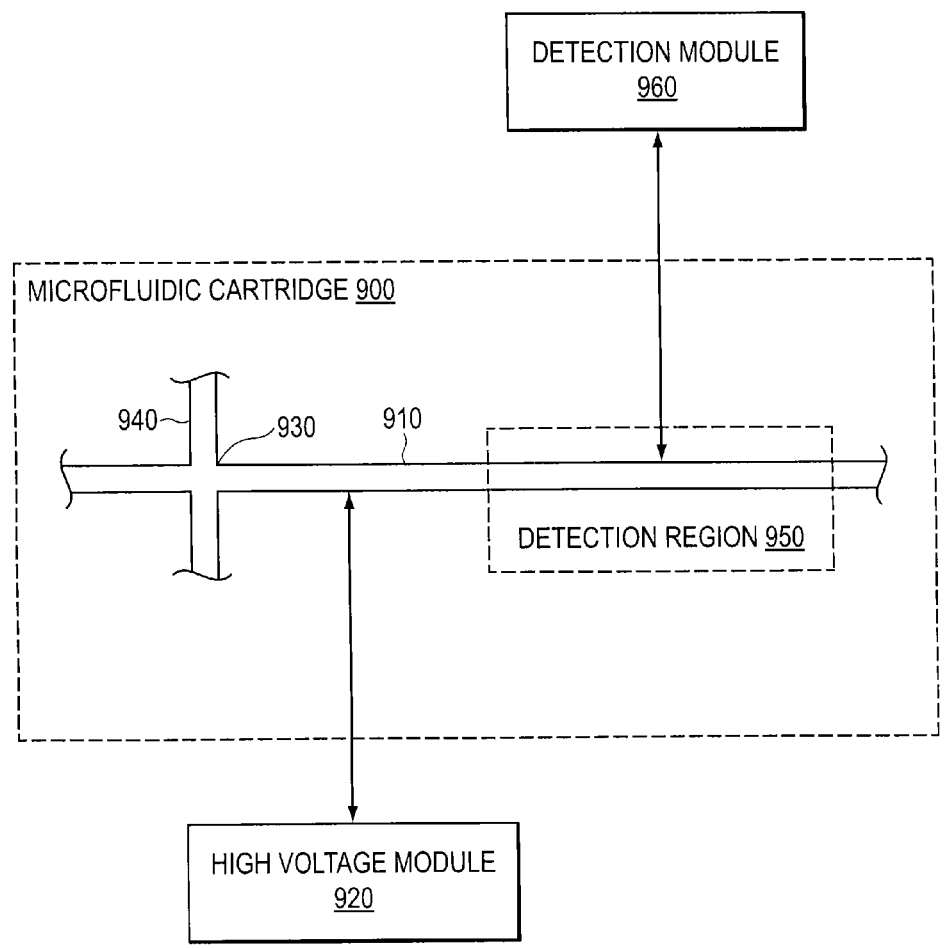
FIG. 9 shows exemplary features for performing nucleic acid separation.

FIG. 9 shows exemplary features for performing nucleic acid separation that can be included within a microfluidic cartridge 900. The on-cartridge features include a separation channel 910. The separation channel 910 can be filled with, for example, a sieving polymer matrix. The sieving polymer matrix can be formed by providing a sieving polymer to the separation channel 910 before nucleic acids are provided to the separation channel 910 for separation. In an embodiment, a nucleic acid mixture, such as a portion of an amplified nucleic acid mixture, can be provided to the separation channel 910. A high voltage module 920 applies high voltage to electrodes (not shown) on the microfluidic cartridge 900 to induce electro-kinetic injection and/or electrophoretic separation. As shown, a T-junction 930 is provided at the beginning of the separation channel 910. The nucleic acid mixture can be provided to the beginning of the separation channel 910 by electro-kinetic injection of a portion of the amplified nucleic acid mixture through a fluidic channel 940.

Before being provided to the separation channel 910, the nucleic acid mixture (or a portion thereof) can be diluted or mixed with one or more separation reagent solutions, such as any of an internal control solution, a dilution solution, and a buffer solution, to improve nucleic acid separation. The nucleic acid mixture (or portion thereof) can be mixed with the separation reagents in a ratio of about 1:1 to about 1:100, such as from about 1:10 to about 1:30 or about 1:15, depending on the concentrations of the reagents. As an example, the nucleic acid mixture can be mixed with an internal control solution that includes an internal lane standard (ILS). The ILS can be used to better ensure accurate size measurements of the nucleic acid fragments. The ILS includes nucleic acids of known size that are used as controls. The internal control solution can also include formamide for denaturing nucleic acids to promote separation. As another example, the nucleic acid mixture can be mixed with an aqueous dilution solution to reduce the ionic strength of the nucleic acid mixture. In order to detect and analyze the separated nucleic acid fragments, the nucleic acid fragments can be labeled prior to separation. The nucleic acid fragments can be labeled during amplification, such as with fluorescent labels. Alternatively, the nucleic acid fragments can be labeled after amplification but prior to separation by mixing the nucleic acid fragments with a dye, such as an intercalating dye (e.g., ethidium bromide). The dye can be included in the internal control solution or another solution.

Once the nucleic acid mixture, such as a portion of an amplified nucleic acid mixture mixed with separation reagents, is provided to the separation channel 910, the nucleic acid fragments within the mixture can be separated. In an embodiment, nucleic acid separation is performed by electrophoresis such that nucleic acid fragments are separated by size. In electrophoresis, the nucleic acid fragments migrate by force of the electric field at different speeds based on the sizes of the nucleic acid fragments. During separation, the separated nucleic acid fragments can be detected through observation of the detection region 950 of the separation channel 910. The detection region 950 can include a detection window configured to enable detection by a laser beam. A detection module 960 is operably coupled to the detection region 950. The detection module 960 can emit a laser beam. The laser beam can be directed to the detection region 950 to excite fluorescent molecules associated with the nucleic acid fragments as they pass through the detection region 950 during nucleic acid separation.

Figure 10:
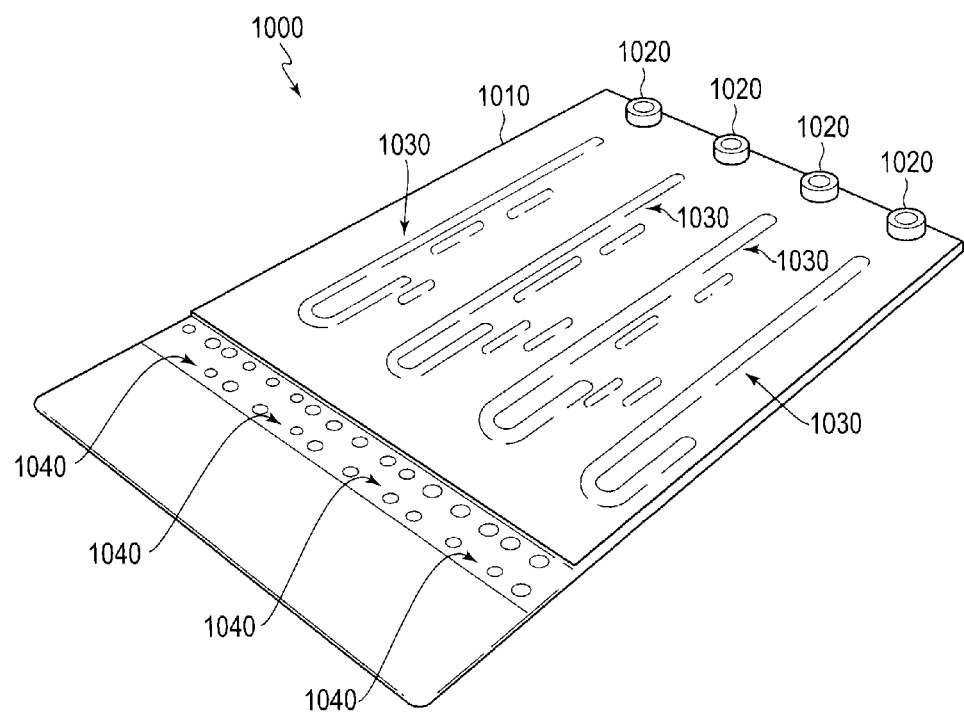
FIG. 10 shows an exemplary microfluidic cartridge and an exemplary sealing layer to be applied over at least a major portion of the microfluidic cartridge.

FIG. 10 shows an exemplary microfluidic cartridge 1000 and an exemplary sealing layer 1010 to be applied over at least a major portion of the microfluidic cartridge 1000. Broadly, the microfluidic cartridge can include one or more sample inputs 1020, one or more fluidic networks 1030, and one or more vent port areas 1040. As shown, four sample inputs 1020, fluidic networks 1030, and vent port areas 1040 are defined in the microfluidic cartridge 1000. The sample inputs 1020 can be configured for fluidic coupling of sample acceptors. The fluidic network 1030 can include features for performing any of nucleic acid extraction, amplification, and separation. Each vent port area 1040 includes a plurality of vent ports that can be configured for coupling to a pressure module of a nucleic acid analyzer to provide hydrodynamic control over liquid within the fluidic networks 1030 during nucleic acid analysis.

The sealing layer 1010 is applied over at least the fluidic networks 1030 of the microfluidic cartridge 1000 to provide a top layer over fluidic network features, including channels, reservoirs, and chambers. In embodiments, the sealing layer 1010 is applied over the sample inputs 1020 and the fluidic networks 1030 or over the entirety of the microfluidic cartridge 1000. The sealing layer 1010 can be in the form of a film and can be pliable. The sealing layer 1010 can be adhered to the surface of the microfluidic cartridge 1000 by heat-driven lamination. In an embodiment, there are two sealing layers that are respectively applied over the top and the bottom of the microfluidic cartridge 100.

The pressure module of the nucleic acid can be configured to independently apply positive and/or negative pressure to individual vent ports to effectuate hydrodynamic movement in performing nucleic acid analysis. Each vent port can be in fluid communication with a discrete feature in the fluidic network 1030 such as to control hydrodynamic movement of liquid with respect to such feature. The vent ports can be coupled to the pressure module through a micro-to-macro interface. The vent ports can be covered with a covering (not shown) that permits the passage of gas (e.g., air) while preventing the passage of liquid. As shown, the vent port areas 1040 are provided on one side of the microfluidic cartridge 1000. Although not necessary, this can generally provide minimal complexity in the micro-to-macro interface with the pressure module of the nucleic acid analyzer. The sealing layer 1010 can also be used to form frangible seals within the fluidic networks 1030.

Figure 11:
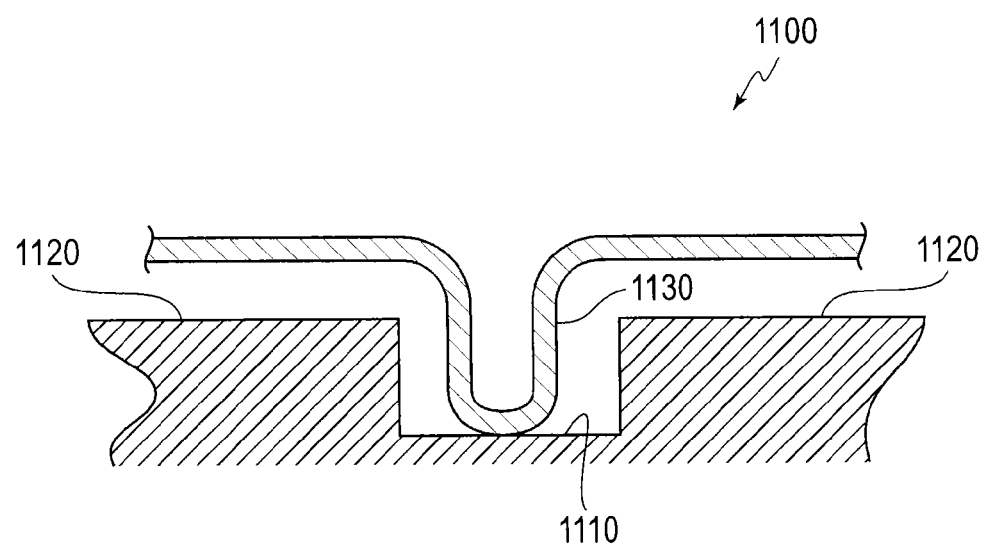
FIG. 11 shows an exemplary frangible seal within a fluidic channel.

FIG. 11 shows an exemplary frangible seal 1100. As shown, the frangible seal 1100 is formed from a depression 1110 defined within a fluidic channel 1120. The depression 1110 has a depth that is greater than the depth of the fluidic channel 1120. However, the depression 1110 can have a depth that is less than the depth of an adjacent reagent reservoir or other chamber. A sealing layer portion 1130 is extended into the depression 1110 such that the sealing layer portion 1130 contacts and is adhered to the base of the depression 1110.

The frangible seal 1100 can be configured to have a predetermined resistance against fluid flow. Fluid flow resistance can be determined by the depth and width of the depression 1110. In general, the frangible seal 1110 has weaker fluid flow resistance as the depression 1110 is made deeper and has greater fluid flow resistance as the depression 1110 is made shallower. A shallower depression 1110 does not stretch the sealing layer portion 1130 as much as a deeper depression 1110 and, thus, a shallower depression 1110 provides more resistance to fluid flow. In embodiments, a fluidic network of a microfluidic cartridge includes frangible seals 1100 having different fluid flow resistances.

For instance, the fluidic network can have frangible seals 1100 that have two different fluid flow resistances. A depression 1110 having a depth of about 2 μm to about 75 μm can be used to form frangible seals 1100 that have sufficient fluid flow resistance to border reagent reservoirs to protect against reagent solution from entering other portions of the fluidic network in the course of loading reagents or operating the microfluidic cartridge until the frangible seals 1100 are intentionally broken by pressure applied by a pressure module. A depression 1110 having a depth of about 2 μm to about 75 μm can be used to form a frangible seal 1100 having a greater fluid flow resistance. The frangible seal 1100 of greater fluid flow resistance can be used in places along the fluidic network where another actuation feature under the control of the pressure module, such as a reusable actuation feature (e.g., a valve), is in close proximity to the location for the frangible seal 1100 of greater fluid flow resistance. A frangible seal 1100 of greater fluid flow resistance is provided in such places to protect against inadvertent seal breakage during operation of the actuation feature.

During operation of the microfluidic cartridge, the frangible seal 1100 can be broken by providing positive or negative pressure of sufficient force through the fluidic channel 1120. Such pressure can cause the sealing layer portion 1130 to detach from the base of the depression 1110. One detached, the sealing layer portion 1130 does not normally reattach to the depression 1110 once pressure is removed. Thus, once broken, the frangible seal 1100 is not automatically reconstituted and represents a one-time actuation feature of the microfluidic cartridge.

Figure 12:
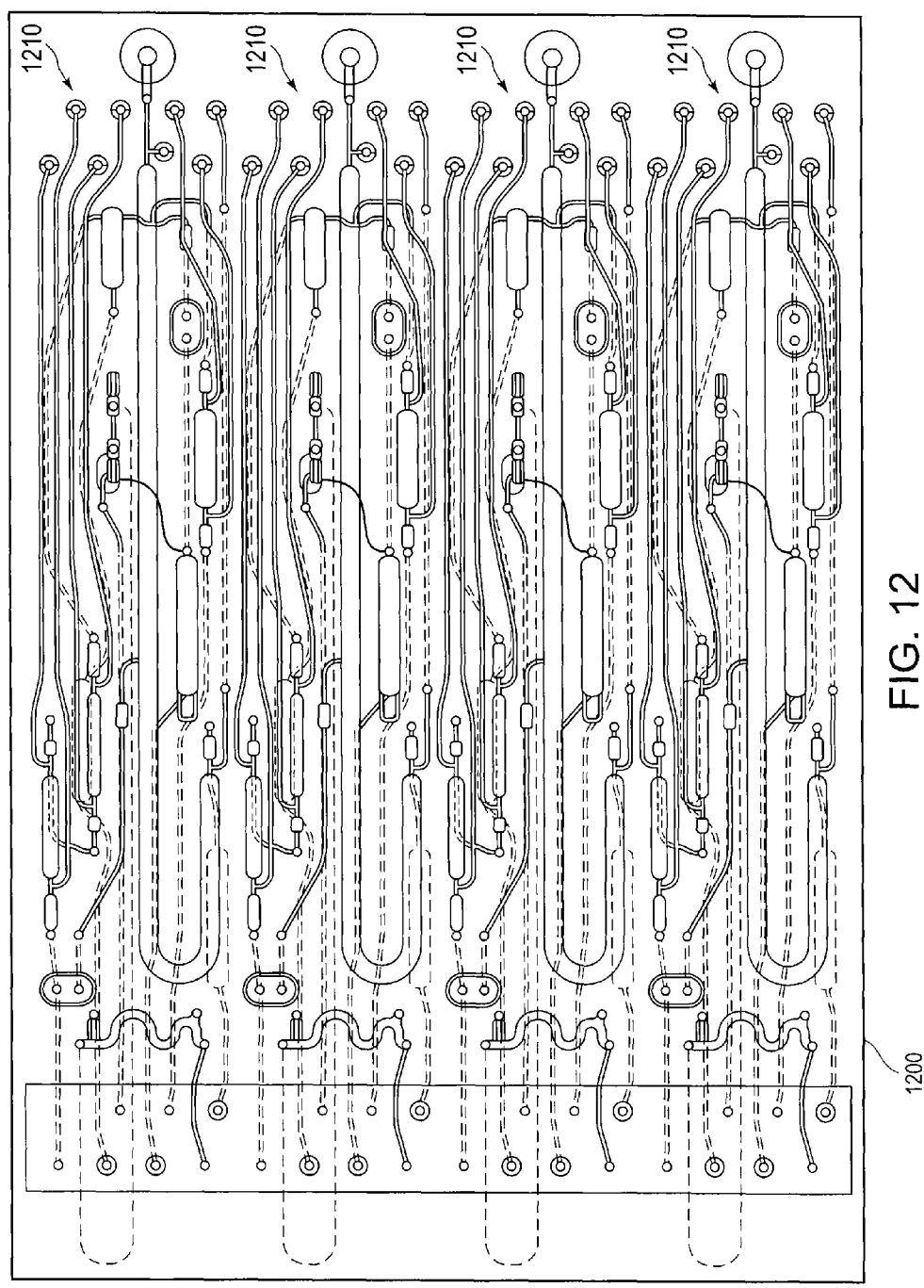
FIG. 12 shows a schematic of an exemplary microfluidic cartridge that combines various features for nucleic acid extraction, nucleic acid amplification, and nucleic acid separation.

FIG. 12 shows a schematic of an exemplary microfluidic cartridge 1200 that combines various features for nucleic acid extraction, nucleic acid amplification, and nucleic acid separation. The microfluidic cartridge 1200 includes four identical nucleic acid analysis portions 1210, in which a biological sample can be analyzed. Accordingly, the nucleic acid analysis may be performed on four different biological samples in parallel or in tandem. In other embodiments, the microfluidic cartridge 1200 can include more or less nucleic acid analysis portions and may only contain a single nucleic acid analysis portion 1210. However, the incorporation of more than one nucleic acid analysis portion 1210 on a microfluidic cartridge 1200 can improve efficiency and/or convenience. Of course, different biological samples can be individually analyzed in the nucleic acid analysis portions 1210. Alternatively, a biological sample can be divided and nucleic acid analysis performed more than once on the same biological sample. Such redundancy can improve accuracy. Further, there is no requirement that all nucleic acid analysis portions 1210 are identical as, for example, nucleic acid analysis portions 1210 on the microfluidic cartridge 1200 can be configured to perform different types of nucleic acid analyses. Alternatively, the individual nucleic acid analysis portions 1210 may be used to perform analyses on unknown samples, positive control samples, negative control samples, or any combination thereof. For instance, a first nucleic acid analysis portion 1210 can be used to analyze an unknown sample and a second nucleic acid analysis portion 1210 can be used to analyze an allelic ladder.

Figure 13:
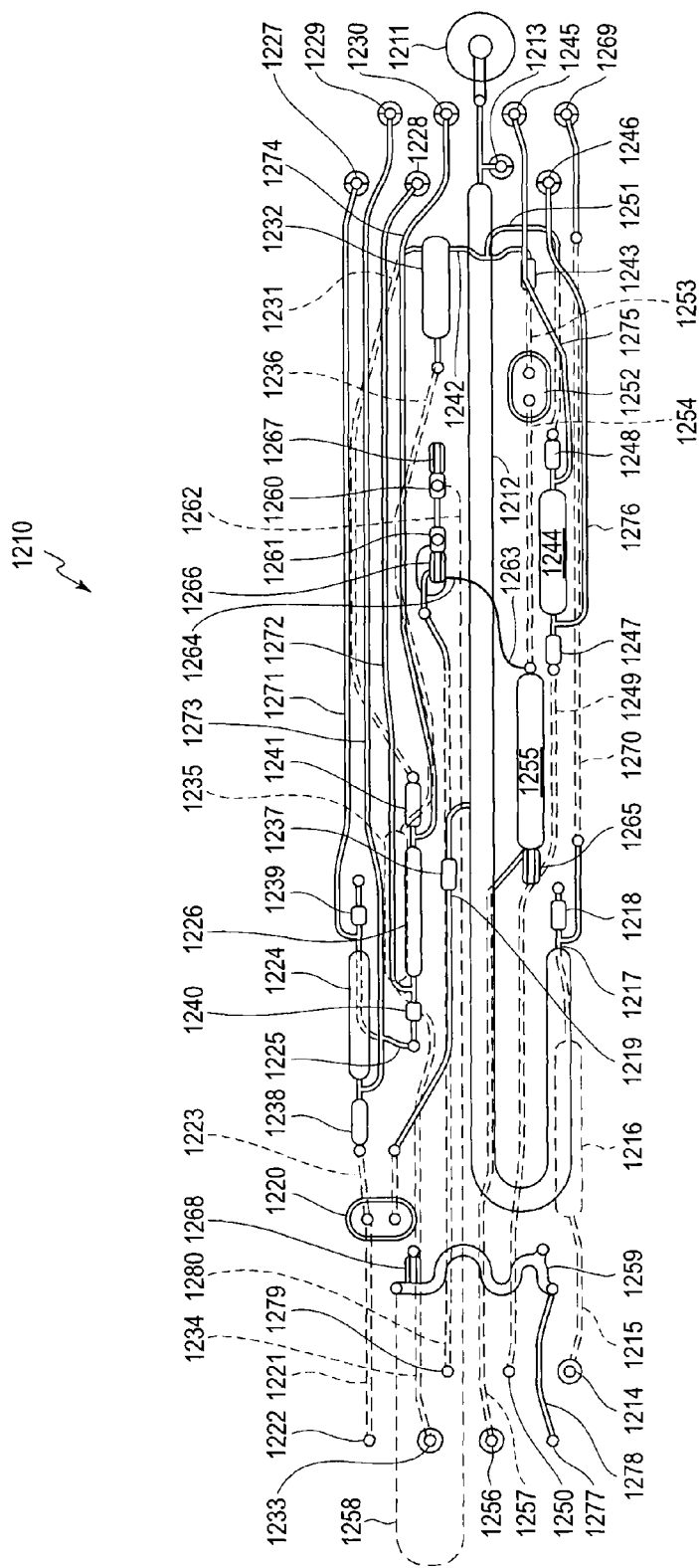
FIG. 13 shows a top view schematic of a nucleic acid analysis portion of the exemplary microfluidic cartridge shown in FIG. 12.
Figure 14:
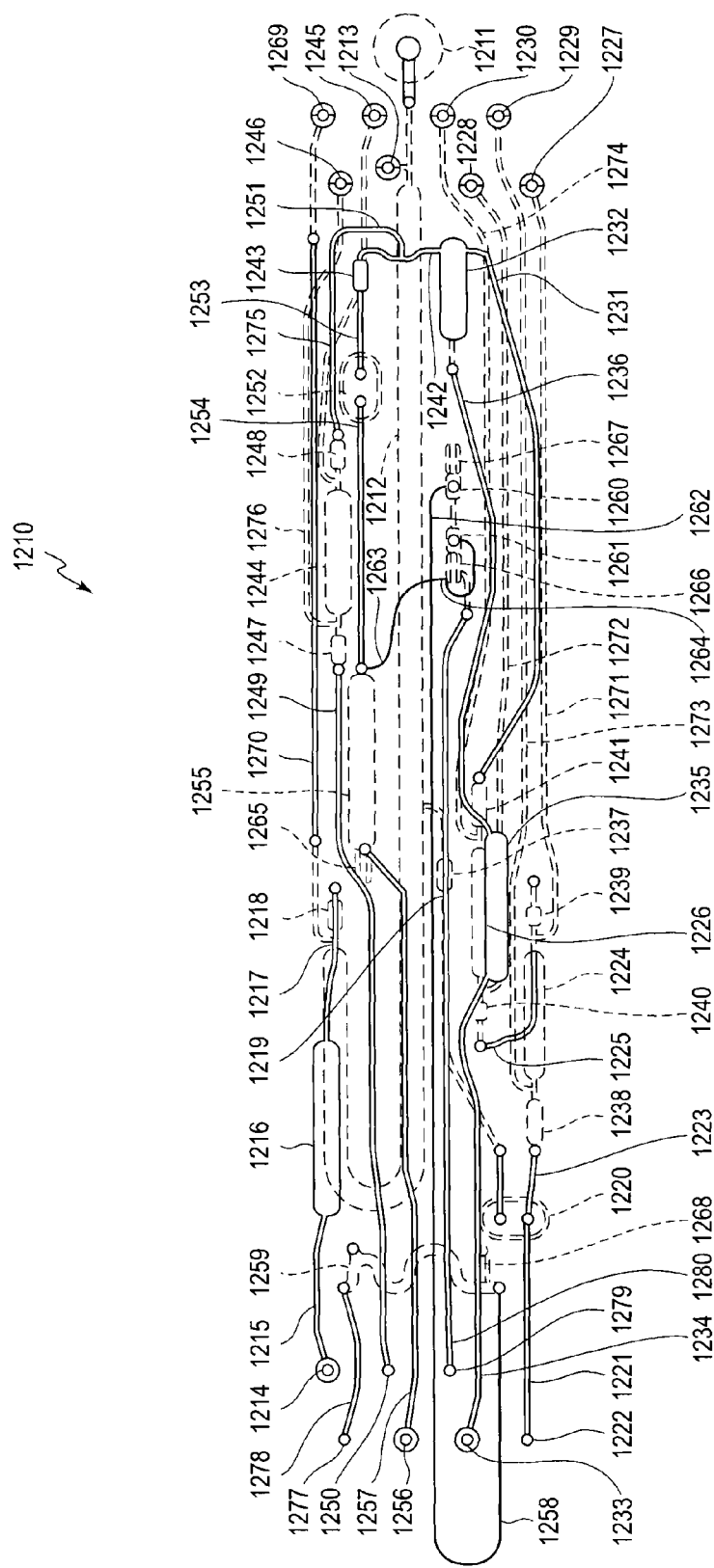
FIG. 14 shows a bottom view schematic of a nucleic acid analysis portion of the exemplary microfluidic cartridge shown in FIG. 12.

FIGS. 13 and 14 show top view and bottom view schematics, respectively, of an exemplary nucleic acid analysis portion 1210 of the microfluidic cartridge 1200 shown in FIG. 12. As shown, the nucleic acid analysis portion 1210 includes nucleic acid extraction features. Specifically, the nucleic acid analysis portion 1210 includes a sample input 1211 configured to be fluidically coupled to a sample acceptor (not shown). The sample input 1211 is in fluid communication with an extraction mixture reservoir 1212. In this embodiment, the extraction mixture reservoir 1212 has a J-shape. In embodiments, the extraction mixture reservoir 1212 can hold from 5 µl to 500 µl of fluid, such as from 50 µl to 300 µl of fluid. In one embodiment, the extraction mixture reservoir 1212 holds about 225 µl of fluid. In other embodiments, the extraction mixture reservoir 1212 can be of a different shape and/or sized to hold more or less fluid. The extraction mixture reservoir 1212 is configured to hold the enzymatic mixture for nucleic acid extraction. The enzymatic mixture can be loaded into the extraction mixture reservoir 1212 through filling port 1213. Gas (e.g., air) that is displaced during loading can exit through port 1269 by way of fluidic channel 1270. Alternatively, the enzymatic mixture reservoir 1212 can be pre-loaded and sealed with the enzymatic mixture. A vent port 1214 is in fluid communication with the extraction mixture reservoir 1212 through a fluidic channel 1215, a chamber 1216, and a fluidic channel 1217. The vent port 1214 is configured to be coupled to a pressure module of a nucleic acid analyzer to effectuate hydrodynamic movement. A seal 1218 is included at one end of the extraction mixture reservoir 1212 to prevent the extraction mixture from entering the channel 1215, the chamber 1216, and the channel 1217. The seal 1218 can be a non-reusable or reusable seal. For example, the seal 1218 is a frangible seal.

During operation, the combination of the extraction mixture reservoir 1212, the sample input 1211, and the sample acceptor (not shown) are used to perform nucleic acid extraction. A pressure module can be configured to provide positive and/or negative pressure to the extraction mixture reservoir 1212 through the channel 1215, the chamber 1216, and the channel 1217. Providing pressure to the extraction mixture reservoir 1212 breaks the seal 1218. Under hydrodynamic control of the pressure module, the enzymatic mixture in the extraction mixture reservoir 1212 and a biological sample in the sample acceptor are contacted and mixed to effectuate nucleic acid extraction. Additionally, an extraction thermal module of a nucleic acid analyzer can be used to heat the enzymatic mixture/biological sample during extraction and to inactivate the enzymes in the enzymatic mixture at the completion of nucleic acid extraction. Upon completion of nucleic acid extraction, the resulting extracted nucleic acid mixture is provided in the extraction mixture reservoir 1212 for further processing. One or more fluidic channels (e.g., 1219) branch from the extraction mixture reservoir 1212 to deliver the sample (or one or more portions thereof) to other features of the nucleic acid analysis portion 1210 of the microfluidic cartridge 1200.

As further shown, the nucleic acid analysis portion 1210 includes nucleic acid amplification features. The fluidic channel 1219 branches from the extraction mixture reservoir 1212. The fluidic channel 1219 continues to a valve 1220. From valve 1220, an aliquot channel 1221 runs to a vent port 1222. The valve 1220 and a vent port 1222 can be operably coupled to a pressure module of a nucleic acid analyzer. During extraction, the valve 1220 can be opened or closed. Another fluidic channel 1223 exits the valve 1220 and is in fluid communication with a first amplification reagent reservoir 1224. Through a connecting fluidic channel 1225, the first amplification reagent reservoir 1224 is in fluid communication with a second amplification reagent reservoir 1226. In other embodiments, the nucleic acid analysis portion 1210 has a single amplification reagent reservoir and, in other embodiments, has more than two amplification reagent reservoirs. The first and second amplification reagent reservoirs 1224, 1226 hold reagents necessary for performing nucleic acid amplification. The amplification reagents are provided to the first and second amplification reagent reservoirs 1224, 1226 through filling ports 1227, 1228 and fluidic channels 1271, 1272, respectively, in fluid communication with off-cartridge stores of amplification reagents. Ports 1229 and 1230 and fluidic channels 1273, 1274 are respectively used to vent air during filling of the first and second amplification reagent reservoirs 1224, 1226. Alternatively, the amplification reagent reservoirs 1224, 1226 can be pre-loaded and sealed with the amplification reagents. As an example, the first and second amplification reagent reservoirs 1224, 1226 respectively hold a DNA polymerase solution and a solution of primers and nucleotides (or vice versa). Through a connecting fluidic channel 1231, the second amplification reagent reservoir 1226 is in fluid communication with a mixing chamber 1232. A vent port 1233 is in fluid communication with the mixing chamber 1232 through a fluidic channel 1234, a chamber 1235, and a fluidic channel 1236. The vent port 1233 is configured to be coupled to a pressure module of a nucleic acid analyzer to effectuate hydrodynamic movement. Through another connecting fluidic channel 1242, the mixing chamber 1232 is in fluid communication with an amplification chamber 1243.

Actuation features are provided along the fluidic network of the nucleic acid analysis portion 1210 of the microfluidic cartridge 1200. For instance, actuation features can be provided along the portion of the fluidic network including the extraction mixture reservoir 1212, the valve 1220, the first and second amplification reagent reservoirs 1224, 1226, and the mixing chamber 1232. The actuation features can be one-time (non-reusable) actuation features, such as frangible seals, which may be of different strengths. As shown, a frangible seal 1237 is provided in the fluidic channel 1219 between the extraction mixture chamber 1212 and the valve 1220. Another frangible seal 1238 is provided in the fluidic channel 1223 between the valve 1220 and the first amplification reagent reservoir 1224. Two frangible seals 1239, 1240 are provided in the fluidic channel 1225 between the first and second amplification reagent reservoirs 1224, 1226. A frangible seal 1241 is also provided in the fluidic channel 1231 between the second amplification reagent reservoir 1226 and the mixing chamber 1232. In an embodiment, the frangible seal 1238 between the valve 1220 and the first amplification reagent reservoir 1224 requires more force to break (i.e., has a greater fluid flow resistance) than the remaining frangible seals.

During operation, the combination of the first and second amplification reagent reservoirs 1224, 1226, the mixing chamber 1232, and the amplification chamber 1243 are used to perform nucleic acid amplification on a portion of the extracted nucleic acid mixture in the extraction mixture reservoir 1223. The vent port 1222 is coupled to a pressure module of a nucleic acid analyzer. A portion of the extracted nucleic acid mixture is moved from the extraction mixture reservoir 1212 to the aliquot channel 1221. The aliquot channel 1221 can be dimensioned to hold the desired amount of the extracted nucleic acid mixture to be provided to the mixing chamber 1232. To move such a portion of the extracted nucleic acid mixture to the aliquot channel 1221, the valve 1220 is opened and the extracted nucleic acid mixture portion is moved (by operation of the pressure module) along the fluidic channel 1219 and through valve 1220. Frangible seal 1237 is broken in the process. As a result, the extracted nucleic acid portion in the aliquot channel 1221 and the respective amplification reagents in the first and second amplification reagent reservoirs 1224, 1226 are separated by the valve 1220 and the frangible seals 1238, 1239, 1240, 1241. Thus, the extracted nucleic acid portion in the aliquot channel 1221, the amplification reagents in the first amplification reagent reservoir 1224, and the amplification reagents in the second amplification reagent reservoir 1226, are separated as discrete liquid volumes. To move the extracted nucleic acid mixture portion volume and the amplification reagent volumes, the frangible seals 1238, 1239, 1240, 1241 are broken under force of the pressure module, and the discrete volumes, in which air separates the discrete volumes, are moved to the mixing chamber 1232.

Further, during operation, the extracted nucleic acid mixture portion and the amplification reagents are mixed in the mixing chamber 1232 to obtain an amplification mixture. During mixing, gas can be vented from a gas vent portion of the mixing chamber 1232 to the environment outside the microfluidic cartridge 1200. After mixing, an amplification mixture is present in the mixing chamber 1232. A portion of the amplification mixture can be provided to the amplification chamber 1243 (by operation of the pressure module) for nucleic acid amplification. In an embodiment, the amplification chamber 1243 is thermal cycled by an amplification thermal module of a nucleic acid analyzer in order to perform PCR. Upon completion of amplification, an amplified nucleic acid mixture is present in the amplification chamber 1243 for further processing. The amplified nucleic acid mixture can contain a mixture of nucleic acid fragments of different size.

As shown, the nucleic acid analysis portion 1210 of the exemplary microfluidic cartridge 1200 includes nucleic acid separation features. An internal control reservoir 1244 is configured to hold an internal control solution for providing an internal control during nucleic acid separation. In embodiments, the internal control solution includes an internal lane standard (ILS). Formamide can also be included to denature nucleic acids in the amplified nucleic acid mixture to facilitate nucleic acid separation. The internal lane control solution is provided to the internal control reservoir 1244 through filling port 1245 and fluidic channel 1275 and air can be vented through fluidic channel 1276 and port 1246. Alternatively, the internal control reservoir 1244 can be pre-loaded and sealed with the internal control solution. Frangible seals 1247, 1248 are provided at opposite ends of the internal control reservoir 1244. A fluidic channel 1249 including frangible seal 1247 extends to a vent port 1250. The vent port 1250 is configured to be coupled to a pressure module of a nucleic acid analyzer to effectuate hydrodynamic movement. The internal control reservoir 1244 is in fluid communication with the amplification chamber 1243 through a fluidic channel 1251 (including frangible seal 1248) that merges with the fluidic channel 1242. The amplification chamber 1243 is fluidically connected to a valve 1252 through a fluidic channel 1253. In use, the valve 1252 is operably coupled to a pressure module of a nucleic acid analyzer. Another fluidic channel 1254 connects the valve 1252 to a sample reservoir 1255. The sample reservoir 1255 is in fluid communication with a vent port 1256 through fluidic channel 1257. The vent port 1256 is configured to be coupled to a pressure module of a nucleic acid analyzer to effectuate hydrodynamic movement.

The nucleic acid analysis portion 1210 further includes a separation channel 1258, a sieving polymer reservoir 1259, a solution reservoir 1260, and a waste reservoir 1261. The sieving polymer reservoir 1259 can be designed to be of any suitable shape. As shown, the sieving polymer reservoir 1259 has more than one bend. As other examples, the sieving polymer reservoir 1259 can have no bends or a single bend, such as to be substantially U-shaped. The sieving polymer reservoir 1259 is in fluid communication with vent port 1277 through fluidic channel 1278. The vent port 1277 is configured to be operably coupled to a pressure module of a nucleic acid analyzer. The waste reservoir 1261 is in fluid communication with vent port 1279, which is configured to be operably coupled to a pressure module of a nucleic acid analyzer, through fluidic channel 1280. The solution reservoir 1260 has a fluidic channel 1262 exiting the solution reservoir 1260 that merges into a first end of the separation channel 1258. The second end of the separation channel 1258 is in fluid communication with the sieving polymer reservoir 1259. A fluidic channel 1263 runs from the sample reservoir 1255 to the waste reservoir 1261. The fluidic channel 1263 can be more constricted (narrow) than other fluidic channels of the nucleic acid analysis portion 1210 to provide reduced volumes to the separation channel 1258. The separation channel 1258 can also be more constricted (narrow) to use reduced volumes for more effective and/or efficient separation. The fluidic channel 1263 intersects the separation channel 1258. Such intersection is at the portion in which the fluidic channel 1262 from the solution reservoir 1260 merges with the separation channel 1258. As shown, the intersection forms a T-junction 1264.

The nucleic acid analysis portion 1210 also includes electrodes 1265, 1266, 1267, 1268. The electrode 1265 borders the sample reservoir 1255 and the electrode 1266 borders the waste reservoir 1261. The electrode 1267 borders the solution reservoir 1260 and the electrode 1268 borders the sieving polymer reservoir 1259. A high voltage module of a nucleic acid analyzer is operably coupled to the electrodes 1265, 1266, 1267, 1268 to apply high voltages to the nucleic acid analysis portion 1210. The electrodes 1265, 1266 are used to perform electro-kinetic injection and the electrodes 1267, 1268 are used to perform electrophoretic separation of nucleic acids. As compared to the voltage applied across electrodes 1265, 1266 to perform electro-kinetic injection, a higher voltage can be applied across electrodes 1267, 1268 to perform electrophoretic separation. The separation channel 1258 can include a detection region. In use, the detection region can be operably coupled to a detection module of a nucleic acid analyzer.

During operation, the separation channel 1258 is used to separate nucleic acid fragments in an amplified nucleic acid mixture. Before separation, a sieving polymer solution is provided from the sieving polymer reservoir 1259 to the separation channel 1258. In the separation channel 1258, the sieving polymer forms a sieving polymer matrix. The internal control solution is provided from the internal control reservoir 1244 to the amplification chamber 1243 through the fluidic channels 1251, 1249. The frangible seals 1247, 1248 are broken in the process. The internal control solution and the amplified nucleic acid mixture are mixed as the internal control solution is provided to the amplification chamber such that the internal control solution becomes part of the amplified nucleic acid mixture. Then, the amplified nucleic acid mixture is moved from the amplification chamber 1243 to the sample reservoir 1255 through opening the valve 1252 and moving the amplified nucleic acid mixture along the channels 1253, 1254. Valve opening and hydrodynamic movement are effectuated by a pressure module of a nucleic acid analyzer.

From the sample reservoir 1255, electro-kinetic injection is performed to inject a portion (i.e., a plug) of the amplified nucleic acid mixture through the fluidic channel 1263 to the T-junction 1264 and into the separation channel 1258. In embodiments, because of the small fluid volumes, it is difficult to determine the exact fraction of the amplified nucleic acid mixture that is injected into the separation channel 1258. Voltage is applied to the electrodes 1265, 1266 from a high voltage module of a nucleic acid analyzer in order to perform electro-kinetic injection. At the T-junction 1264, the injected portion is mixed with a solution supplied from the solution reservoir 1260 to the T-junction 1264 through the fluidic channel 1262. The solution can be a dilution and/or buffer solution. Some of the amplified nucleic acid mixture and/or solution may cross the T-junction 1264 and not enter into the separation channel 1258. Such liquid is collected in the waste reservoir 1261. Electrophoresis is performed in the separation channel 1258 to separate nucleic acid fragments by size. Voltage is applied to the electrodes 1267, 1268 to generate an electric field for performing electrophoretic separation of nucleic acids. The separated nucleic acid fragments are detected in the detection region by a detection module of a nucleic acid analyzer.

As discussed above, the detection module can include an optical unit for detecting labeled nucleic acid fragments. The optical unit can include a self-calibrating array of confocal optical components. The self-calibrating optical unit can perform calibration in conjunction with an alignment dye. Calibration can be performed before detection of the separated nucleic acids and can be performed after the sieving polymer solution is provided from the sieving polymer reservoir 1259 to the separation channel 1258. The alignment dye can be loaded into the sieving polymer reservoir 1259 with the sieving polymer solution and provided to the separation channel 1258 before nucleic acid separation is performed. The self-calibrating optical module, under control of the controller module, can scan the detection region of the separation channel 1258 for the most optimal signal from the alignment dye and the system can be adjusted to accept a maximum intensity. The alignment dye can absorb and emit light at wavelengths optically distinct from one or more labels or dyes used to label the nucleic acids to be separated. As examples, the alignment dye can be a fluorescent dye, a high-wavelength dye, an infrared dye, an ultraviolet dye, or a sub-ultraviolet dye.

Figure 15:
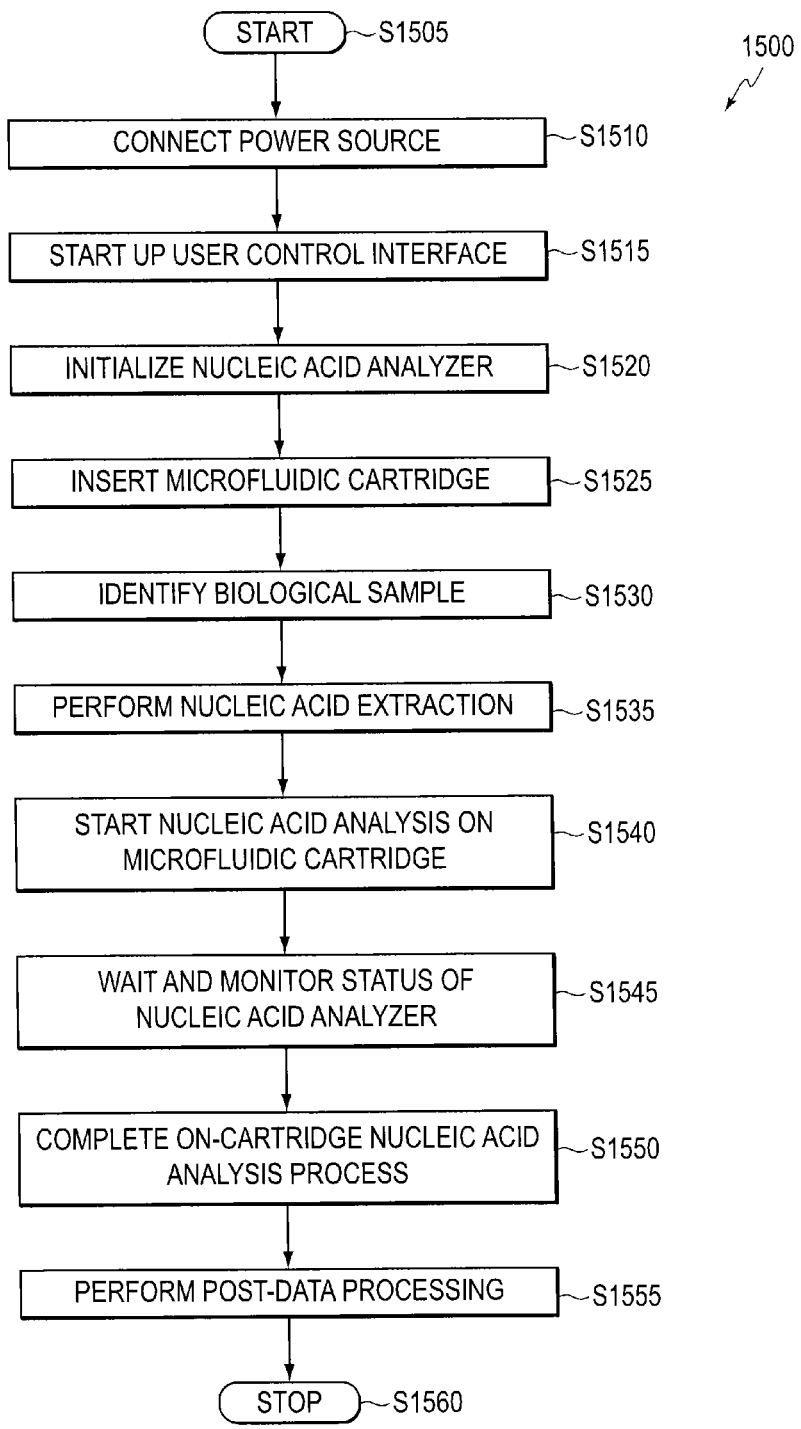
FIG. 15 shows a flow chart outlining an exemplary process for using a nucleic acid analyzer to perform nucleic acid analysis.

FIG. 15 shows a flow chart outlining an exemplary process 1500 for using a nucleic acid analyzer to perform nucleic acid analysis. The process starts at S1505 and finishes at S1560.

At S1510, the nucleic acid analyzer is connected to (e.g., plugged into) a main power supply. In an embodiment, the main power supply can be a 110 V, 50 Hz, AC power supply, or can be a 220 V, 60 Hz, AC power supply. The power module can convert the main power supply to a plurality of operation powers and provide the plurality of operation powers to various modules/components of the nucleic acid analyzer. Then, the process proceeds to S1515.

At S1515, the user starts up a user control interface. For example, the user turns on a computing module to start a software package that interacts with the user and a controller module. The software package enables the computing module to provide a user control interface on a display. Further, the software package enables the computing module to receive user instructions via a user input device, such as a touchscreen, keyboard, or mouse. The software package can also enable the computing module to communicate with a controller module. Then, the process proceeds to S1520.

At S1520, the user instructs the nucleic acid analyzer to initialize. The user control interface receives the initialization instructions and the software package enables the computing module to send the initialization instructions to the controller module. The controller module can then initialize the various components of the nucleic acid analyzer. For example, the controller module can power on the various components, check the status, and reset the status if needed. Then, the process proceeds to S1525.

At S1525, the user inserts the microfluidic cartridge (optionally already coupled to a sample acceptor) in the nucleic acid analyzer. The interface components can suitably couple the microfluidic cartridge to other components of the nucleic acid analyzer. Then, the process proceeds to S1530.

At S1530, the nucleic acid analyzer can identify the biological sample. In an example, the nucleic acid analyzer includes a radio frequency identification (RFID) reader or a barcode reader that can read an RFID tag or barcode on the sample acceptor for identifying the biological sample. Then, the process proceeds to S1535.

At S1535, nucleic acid extraction can be performed. The resulting extracted nucleic acid mixture is received in the extraction mixture chamber of a nucleic acid analysis portion of the microfluidic cartridge for further processing. Then, the process proceeds to S1540.

At S1540, nucleic acid analysis can be started. The user can instruct the nucleic acid analyzer to further process the extracted nucleic acid mixture or the nucleic acid analyzer can automatically begin further processing of the extracted nucleic acid mixture. The controller module can perform a control procedure for nucleic acid analysis. In an example, the controller module performs a short tandem repeat (STR) typing procedure corresponding to a multiplexed STR typing analysis. In another example, the controller module performs a sequencing procedure corresponding to a nucleic acid sequencing analysis. Then, the process proceeds to S1545.

At S1545, the user waits and can monitor the status of the nucleic acid analysis. The control procedure can specify sequences and timings of control signals to various components of the nucleic acid analyzer to perform the nucleic acid analysis process. Then, the controller module automatically sends the control signals according to the sequences and the timings specified in the control procedure. In addition, the controller module receives status and feedback signals from the various components and sends them to the computing module. The computing module can then provide the analysis status for the user to monitor. Then, the process proceeds to S1550.

At S1550, the on-cartridge nucleic acid analysis process can be completed. The controller module can finish executing the control procedure and can send an analysis-completed status to the computing module. Data generated upon completion of the nucleic acid analysis can be made available for post-data processing. The computing module can inform the user of the analysis-completed status via the user control interface. Then, the process proceeds to S1555.

At S1555, post-data processing can be performed. For example, the user can instruct that the nucleic acid analysis data be stored and/or transmitted to a remote receiver. In addition, the user may start a software package for post-data processing. Alternatively, the software package for post-data processing can be suitably integrated with the control procedure. Thus, after the control procedure is successfully executed, the software package for post-data processing is automatically executed to perform post-data processing. Then, the process terminates at S1560. In embodiments, steps of the process may be repeated. For instance, any of S1525-1555 can be performed multiple times using a different microfluidic cartridge. Any of S1530-S1555 can be performed multiple times using a different nucleic acid analysis portion on the same microfluidic cartridge.

Figure 16:
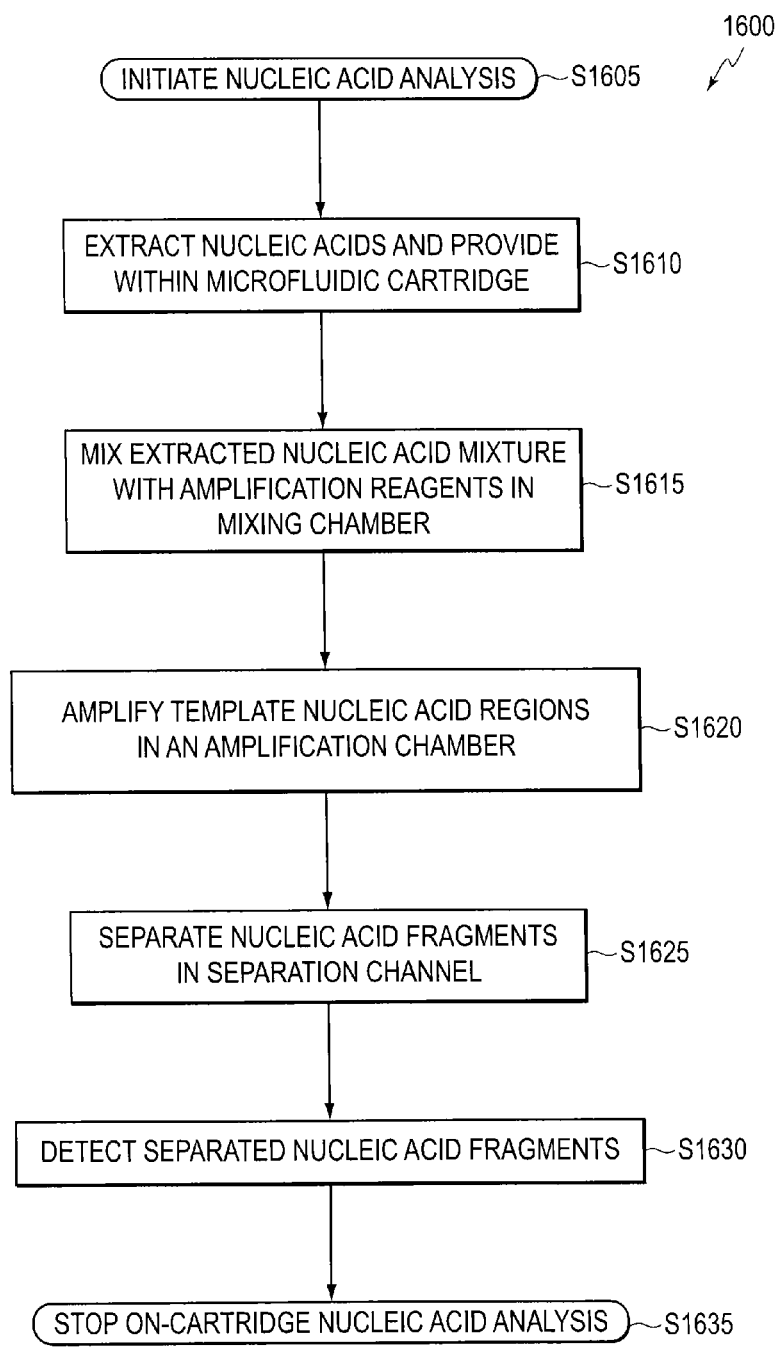
FIG. 16 shows a flow chart outlining an exemplary on-cartridge process for a microfluidic cartridge operably coupled to a nucleic acid analyzer.

FIG. 16 shows a flow chart outlining an exemplary on-cartridge process 1600 for a microfluidic cartridge operably coupled to a nucleic acid analyzer. The process starts at S1605 and proceeds to S1635. At S1605, nucleic acid analysis is initiated. The microfluidic cartridge can be operably coupled to a sample acceptor as well as to the nucleic acid analyzer. The sample acceptor can hold a biological sample for analysis. Then, the process proceeds to S1610.

At S1610, nucleic acids are extracted from the biological sample to provide an extracted nucleic acid mixture within the microfluidic cartridge. The biological sample can be presented for extraction by the sample acceptor. The biological sample can be contacted with an enzymatic mixture from an extraction mixture reservoir to extract nucleic acids from the biological sample. Extraction can be performed at a first temperature. A second higher temperature can be applied to inactivate enzymes in the enzymatic mixture to conclude nucleic acid extraction. After extraction, the extracted nucleic acid mixture can be held in the extraction mixture reservoir. Then, the process proceeds to S1615.

At S1615, the extracted nucleic acid mixture (or a portion thereof) is mixed with amplification reagents in a mixing chamber of the microfluidic cartridge. The extracted nucleic acid mixture (or portion thereof) can be provided to the mixing chamber, along with the amplification reagents, using the fluidic network of the microfluidic cartridge. The extracted nucleic acid mixture (or portion thereof) and the amplification reagents can be mixed in the mixing chamber to obtain an amplification mixture. During mixing, gas can be vented from the mixing chamber. Then, the process proceeds to S1620.

At S1620, template nucleic acid regions (sequences) of the nucleic acids in the amplification mixture are amplified in an amplification chamber of the microfluidic cartridge to obtain an amplified nucleic acid mixture. The amplification mixture can be provided to the amplification chamber using the fluidic network of the microfluidic cartridge. In the amplification chamber, the amplification mixture is placed under reaction conditions to amplify template nucleic acid sequences. In an embodiment, the amplification chamber is used to perform PCR. To perform PCR, the amplification chamber is thermal cycled. During amplification, the amplified nucleic acids can be tagged with labels, such as fluorescent labels. Then, the process proceeds to S1625.

At S1625, nucleic acid fragments in the amplified nucleic acid mixture are separated in a separation channel of the microfluidic cartridge to obtain separated nucleic acid fragments. A portion of the amplified nucleic acid mixture can be provided to the separation channel through the fluidic network of the microfluidic cartridge. Before being providing to the separation channel, the portion of amplified nucleic acid mixture can be mixed with one or more solutions, such as an internal control, dilution, and/or buffer solutions. A solution can include an ILS and may include an intercalating dye if the nucleic acid fragments have not been previously labeled. A solution can reduce the ionic strength of the amplified nucleic acid mixture portion. Once the portion of the amplified nucleic acid mixture is provided to the separation channel, the nucleic acid fragments are separated as they migrate along the length of the separation channel. In an embodiment, nucleic acid separation is performed by DNA electrophoresis such that the DNA fragments are separated by size. An electric field induces the DNA fragments to migrate along the length of the separation channel. The process then proceeds to S1630.

At S1630, the separated nucleic acid fragments are detected within a detection region of the separation channel of the microfluidic cartridge as the nucleic acid fragments pass through the detection region in order to generate nucleic acid analysis data for further processing by the nucleic acid analyzer. The nucleic acid fragments can be detected by a detection module of the nucleic acid analyzer. The detection region of the microfluidic cartridge can include a detection window that enables detection of the nucleic acid fragments. Fluorescent molecules associated with the nucleic acid fragments can be excited by a laser beam emitted from a laser source unit of the detection module. In an embodiment, the nucleic acid fragments are labeled for multicolor fluorescence detection. A set of optics of can collect and direct the fluorescent signals to a detection unit of the detection module. The detection unit can convert the detected fluorescence into data for processing by a controller module. Then, the on-cartridge process terminates at S1635.

While the invention has been described in conjunction with the specific exemplary embodiments thereof, it is evident that many alternatives, modifications, and variations will be apparent to those skilled in the art. Accordingly, exemplary embodiments of the invention as set forth herein are intended to be illustrative, not limiting. There are changes that may be made without departing from the spirit and scope of the invention.

What is claimed is:

1. A nucleic acid analyzer, comprising:
a microfluidic cartridge module configured to accept at least one microfluidic cartridge comprising:
- at least one nucleic acid analysis portion, each nucleic acid analysis portion including:
  - a fluidic network defined within the nucleic acid analysis portion, the fluidic network being configured for micro-liter volumes or less, the fluidic network including at least one frangible seal formed from a depression defined in a fluidic channel with a fluid flow resistance determined by a depth and a width of the depression;
  - a sample input at a beginning of the fluidic network, the sample input having a fitting that is configured to be mated to a complementary fitting of a sample acceptor to form a fluid-tight seal;
  - a plurality of vent ports and fluidic channels in the fluidic network configured to effectuate hydrodynamic movement within the fluidic network;
  - an extraction mixture reservoir in the fluidic network, the extraction mixture reservoir being configured to hold an enzymatic mixture for performing nucleic acid extraction on a sample provided by the sample acceptor;
  - a mixing chamber in the fluidic network, the mixing chamber being configured to mix amplification reagents and a portion of an extracted nucleic acid mixture; and
- an amplification chamber in the fluidic network, the amplification chamber being configured to hold an amplification mixture during nucleic acid amplification;
a pressure module configured to be coupled to the plurality of vent ports to effectuate hydrodynamic movement within the fluidic network of the microfluidic cartridge;
an extraction thermal module configured to impart temperatures to any of the microfluidic cartridge and the sample acceptor during nucleic acid extraction;
an amplification thermal module configured to impart temperatures to the microfluidic cartridge during nucleic acid amplification;
a high voltage module configured to apply high voltages on the microfluidic cartridge;
a power module configured to provide operation powers to the nucleic acid analyzer;
a detection module configured to detect labeled or dyed nucleic acids; and
a controller module configured to control the pressure module, the extraction thermal module, the amplification thermal module, the high voltage module, the power module, and the detection module according to a control procedure.

2. The nucleic acid analyzer of claim 1, wherein the pressure module is configured to break one or more frangible seals in the fluidic network and/or actuate one or more valves of the microfluidic cartridge during nucleic acid analysis.

3. The nucleic acid analyzer of claim 1, wherein the pressure module is configured to provide pneumatic positive and/or negative pressure.

4. The nucleic acid analyzer of claim 1, wherein the pressure module includes a hydrodynamic pressure/vacuum system.

5. The nucleic acid analyzer of claim 1, wherein the pressure module includes a solenoid manifold.

6. The nucleic acid analyzer of claim 1, wherein the extraction thermal module is configured to heat the sample acceptor by contact heating.

7. The nucleic acid analyzer of claim 1, wherein the amplification thermal module includes a non-contact heating unit and a temperature sensing unit.

8. The nucleic acid analyzer of claim 7, wherein the non-contact heating unit includes an infrared light source.

9. The nucleic acid analyzer of claim 7, wherein the temperature sensing unit includes an infrared pyrometer to measure temperature of a portion of the microfluidic cartridge.

10. The nucleic acid analyzer of claim 1, wherein the detection module comprises:
- a laser source unit configured to emit a laser beam;
- a detector unit configured to detect fluorescence; and
- an optical unit configured to direct the laser beam to a separation channel to excite fluorescent molecules to emit fluorescence and to then direct fluorescence to the detector unit for detection.

11. The nucleic acid analyzer of claim 10, wherein the optical unit includes a self-calibrating array of confocal optical components configured to perform calibration in conjunction with an alignment dye.

12. The nucleic acid analyzer of claim 1, further comprising a computing module operationally coupled to the controller module, the computing module having a user interface.

* * * * *